United States Patent
Cipollone et al.

(10) Patent No.: US 9,962,512 B2
(45) Date of Patent: May 8, 2018

(54) METHODS, SYSTEMS AND DEVICES FOR NON-INVASIVE VENTILATION INCLUDING A NON-SEALING VENTILATION INTERFACE WITH A FREE SPACE NOZZLE FEATURE

(75) Inventors: Joseph Cipollone, San Ramon, CA (US); Joey Aguirre, San Ramon, CA (US); Todd Allum, Livermore, CA (US); Darius Eghbal, Oakland, CA (US); Anthony D. Wondka, Thousand Oaks, CA (US)

(73) Assignee: Breathe Technologies, Inc. CA (US)

( * ) Notice: Subject to any disclaimer, the term of this patent is extended or adjusted under 35 U.S.C. 154(b) by 689 days.

(21) Appl. No.: 12/876,099

(22) Filed: Sep. 3, 2010

(65) Prior Publication Data
US 2011/0094518 A1   Apr. 28, 2011

Related U.S. Application Data

(63) Continuation-in-part of application No. 12/753,846, filed on Apr. 2, 2010, now Pat. No. 9,675,774, and a
(Continued)

(51) Int. Cl.
*A61M 16/00* (2006.01)
*A61M 16/06* (2006.01)
(Continued)

(52) U.S. Cl.
CPC .... *A61M 16/0666* (2013.01); *A61M 16/0677* (2014.02); *A61M 16/0683* (2013.01);
(Continued)

(58) Field of Classification Search
CPC .. A61M 16/00; A61M 16/06; A61M 16/0666; A61M 16/0672; A61M 16/0677;
(Continued)

(56) References Cited

U.S. PATENT DOCUMENTS

| 50,641 A | 10/1865 | Stone |
|---|---|---|
| 428,592 A | 5/1890 | Chapman |

(Continued)

FOREIGN PATENT DOCUMENTS

| CN | 1455690 | 11/2003 |
|---|---|---|
| CN | 1455690 A | 11/2003 |

(Continued)

OTHER PUBLICATIONS

Saslow et al. Work of breathing using high-flow nasal cannula in preterm infants, Journal of Perinatology (2006) 26, 476-480.*
(Continued)

*Primary Examiner* — (Jackie) Tan-Uyen T Ho
*Assistant Examiner* — Joseph D Boecker
(74) *Attorney, Agent, or Firm* — Stetina Brunda Garred and Brucker; Mark B. Garred

(57) ABSTRACT

A system for supplying ventilatory support may include a nasal interface configured to communicate with a patient's nose while allowing the patient to breathe ambient air directly without flowing through the nasal interface. A nozzle may be associated with the nasal interface at a distance from a nose. The nozzle may be connectable to the gas delivery circuit and the gas delivery source. The nozzle may be capable of delivering gas into the nasal passage by creating negative pressure area near the nozzle and a positive pressure area near the entrance to the nose. A combination of gas from the gas delivery source and air entrained from the gas exiting the nozzle may provide ventilatory support.

66 Claims, 20 Drawing Sheets

Related U.S. Application Data continuation-in-part of application No. 12/753,851, filed on Apr. 2, 2010, now Pat. No. 9,180,270, and a continuation-in-part of application No. 12/753,854, filed on Apr. 2, 2010, and a continuation-in-part of application No. 12/753,856, filed on Apr. 2, 2010, now Pat. No. 9,227,034, and a continuation-in-part of application No. PCT/US2010/029871, filed on Apr. 2, 2010, and a continuation-in-part of application No. 12/753,853, filed on Apr. 2, 2010, and a continuation-in-part of application No. PCT/US2010/029873, filed on Apr. 2, 2010, and a continuation-in-part of application No. PCT/US2010/029874, filed on Apr. 2, 2010, and a continuation-in-part of application No. PCT/US2010/029875, filed on Apr. 2, 2010.

(60) Provisional application No. 61/239,728, filed on Sep. 3, 2009, provisional application No. 61/255,760, filed on Oct. 28, 2009, provisional application No. 61/294,363, filed on Jan. 12, 2010, provisional application No. 61/306,370, filed on Feb. 19, 2010, provisional application No. 61/166,150, filed on Apr. 2, 2009.

(51) Int. Cl.
*A61M 16/08* (2006.01)
*A61M 16/10* (2006.01)
*A61M 16/12* (2006.01)
*A61M 16/16* (2006.01)
*A61M 16/20* (2006.01)

(52) U.S. Cl.
CPC .... *A61M 16/0688* (2014.02); *A61M 16/0858* (2014.02); *A61M 16/101* (2014.02); *A61M 16/127* (2014.02); *A61M 16/085* (2014.02); *A61M 16/0833* (2014.02); *A61M 16/16* (2013.01); *A61M 16/208* (2013.01); *A61M 2016/0021* (2013.01); *A61M 2016/0024* (2013.01); *A61M 2202/0208* (2013.01); *A61M 2202/03* (2013.01); *A61M 2205/17* (2013.01); *A61M 2205/8206* (2013.01)

(58) Field of Classification Search
CPC .......... A61M 16/0683; A61M 16/0688; A61M 16/101; A61M 16/127; A61M 2202/0208
See application file for complete search history.

(56) References Cited

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,245,969 A * | 6/1941 | Francisco et al. ....... 128/207.18 |
| 2,259,817 A | 10/1941 | Hawkins |
| 2,499,650 A | 3/1950 | Kaslow |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A * | 4/1960 | Sheridan ........... A61M 16/0666 128/207.18 |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,400,714 A * | 9/1968 | Sheridan ........... A61M 16/0666 128/207.18 |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Stayer |
| 4,393,869 A | 7/1983 | Boyarsky et al. |
| 4,406,283 A * | 9/1983 | Bir ................... A61M 16/0666 128/207.18 |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |

(56) References Cited

U.S. PATENT DOCUMENTS

| | | |
|---|---|---|
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |

(56) References Cited

U.S. PATENT DOCUMENTS

| | | |
|---|---|---|
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |

(56) References Cited

U.S. PATENT DOCUMENTS

| | | |
|---|---|---|
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | Devries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | Devries et al. |
| 7,188,624 B2 | 3/2007 | Wood |
| 7,195,016 B2 | 3/2007 | Loyd et al. |

(56) References Cited

U.S. PATENT DOCUMENTS

| | | |
|---|---|---|
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 8,240,309 B2 * | 8/2012 | Doshi et al. ............ 128/207.18 |
| 9,132,250 B2 * | 9/2015 | Allum .................. A61M 16/00 |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 * | 2/2002 | Hickle ................ A61B 5/0836 |
| | | 128/204.22 |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |

(56) References Cited

U.S. PATENT DOCUMENTS

| | | |
|---|---|---|
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0016432 A1* | 1/2004 | Genger ................ A61M 16/00 128/204.18 |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1* | 11/2004 | Gunaratnam ..... A61M 16/0666 128/207.18 |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005936 A1* | 1/2005 | Wondka ................ 128/204.18 |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0205098 A1* | 9/2005 | Lampotang et al. .... 128/207.18 |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107727 A1* | 5/2007 | Brichetto ................ A62B 7/14 128/204.18 |
| 2007/0107728 A1 | 5/2007 | Ricciardelli et al. |
| 2007/0107732 A1 | 5/2007 | Dennis et al. |
| 2007/0107737 A1* | 5/2007 | Landis .............. A61M 16/0666 128/207.18 |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272247 A1* | 11/2007 | Porat ................ A61M 16/0666 128/206.28 |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunarathnam et al. |
| 2008/0092905 A1 | 4/2008 | Gunarathnam et al. |
| 2008/0092906 A1 | 4/2008 | Gunarathnam et al. |
| 2008/0099024 A1 | 5/2008 | Gunarathnam et al. |
| 2008/0099027 A1 | 5/2008 | Gunarathnam et al. |
| 2008/0105264 A1 | 5/2008 | Gunarathnam et al. |
| 2008/0110462 A1 | 5/2008 | Chekal et al. |
| 2008/0121230 A1 | 5/2008 | Cortez et al. |
| 2008/0135044 A1* | 6/2008 | Freitag et al. ........... 128/200.26 |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0173311 A1* | 7/2008 | Miller et al. .............. 128/207.18 |

(56) References Cited

U.S. PATENT DOCUMENTS

| | | |
|---|---|---|
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0043801 A1* | 2/2010 | Hailing ............ A61M 16/0666 128/207.18 |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |
| 2013/0092165 A1* | 4/2013 | Wondka ................ A61M 15/08 128/204.25 |
| 2016/0213281 A1* | 7/2016 | Eckerbom ......... A61M 16/0672 |

FOREIGN PATENT DOCUMENTS

| | | |
|---|---|---|
| CN | 1905917 | 1/2007 |
| CN | 101365508 | 2/2009 |
| CN | 101365508 A | 2/2009 |
| DE | 19626924 | 1/1998 |
| DE | 29902267 U1 | 7/1999 |

(56) References Cited

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| FR | 2827778 | 1/2003 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| JP | 2007518451 | 7/2007 |
| JP | 2009160403 | 7/2009 |
| WO | WO-1992/11054 | 7/1992 |
| WO | WO-1998/01176 | 1/1998 |
| WO | WO-1999/04841 | 2/1999 |
| WO | WO-2000/064521 | 11/2000 |
| WO | WO-2001/076655 | 10/2001 |
| WO | WO 2002/062413 | 8/2002 |
| WO | WO03068301 | 8/2003 |
| WO | WO-2004/009169 | 1/2004 |
| WO | 2004105846 | 12/2004 |
| WO | WO2005007056 | 1/2005 |
| WO | WO-2005/014091 | 2/2005 |
| WO | WO 2005/014091 | 2/2005 |
| WO | WO2005011556 | 2/2005 |
| WO | WO 2005/018524 | 3/2005 |
| WO | WO-2005/018524 | 3/2005 |
| WO | 2006088007 | 8/2006 |
| WO | WO-2006/138580 | 12/2006 |
| WO | WO-2007/035804 | 3/2007 |
| WO | WO 2007/035804 | 3/2007 |
| WO | WO-2007/139531 | 12/2007 |
| WO | WO 2007/142812 | 12/2007 |
| WO | WO-2007142812 | 12/2007 |
| WO | WO-2008/014543 | 2/2008 |
| WO | WO 2008/019102 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO 2008/144589 | 11/2008 |
| WO | WO-2008/144589 | 11/2008 |
| WO | WO 2008/144669 | 11/2008 |
| WO | WO-2008/144669 | 11/2008 |
| WO | WO-2009/042973 | 4/2009 |
| WO | WO 2009/042973 | 4/2009 |
| WO | WO 2009/042974 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO 2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO 2009/129506 | 10/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO 2009/151791 | 12/2009 |
| WO | WO-2010/000135 | 1/2010 |
| WO | WO-2010/021556 | 2/2010 |
| WO | WO-2010/022363 | 2/2010 |
| WO | WO 2010/022363 | 2/2010 |
| WO | WO 2010/039989 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO 2010/099375 | 9/2010 |
| WO | WO-2010/102094 | 9/2010 |
| WO | WO 2011/029073 | 9/2010 |
| WO | WO 2010/115166 | 10/2010 |
| WO | WO 2010/115168 | 10/2010 |
| WO | WO 2010/115169 | 10/2010 |
| WO | WO 2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO 2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO 2011/029073 | 3/2011 |
| WO | WO 2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | PCT/US11/47994 | 8/2011 |
| WO | PCT/US11/54446 | 9/2011 |
| WO | WO-2011/112807 | 9/2011 |

OTHER PUBLICATIONS

U.S. Appl. No. 11/523,518, filed Sep. 20, 2006, Freitag et al, Abandoned.
U.S. Appl. No. 13/211,248, filed Aug. 16, 2011, Wondka et al., Pending.
U.S. Appl. No. 13/251,070, filed Sep. 30, 2011, Wondka et al., Pending.
U.S. Appl. No. 29/388,700, filed Mar. 31, 2011, Eghbal et al., Pending.
U.S. Appl. No. 60/479,213, filed Jun. 18, 2003, Wondka, Expired.
U.S. Appl. No. 60/495,812, filed Aug. 18, 2003, Wondka, Expired.
U.S. Appl. No. 60/511,820, filed Oct. 14, 2003, Wondka, Expired.
U.S. Appl. No. 60/586,453, filed Jul. 9, 2004, Wondka, Expired.
U.S. Appl. No. 60/718,318, filed Sep. 20, 2005, Freitag et al., Expired.
U.S. Appl. No. 60/801,104, filed May 18, 2006, Freitag, Expired.
U.S. Appl. No. 60/835,066, filed Aug. 3, 2006, Freitag et al., Expired.

(56) References Cited

OTHER PUBLICATIONS

U.S. Appl. No. 60/924,514, filed May 18, 2007, Wondka et al., Expired.
U.S. Appl. No. 60/960,362, filed Sep. 26, 2007, Wondka et al., Expired.
U.S. Appl. No. 60/960,370, filed Sep. 26, 2007, Wondka et al., Expired.
U.S. Appl. No. 61/006,548, filed Jan. 18, 2008, Wondka et al., Expired.
U.S. Appl. No. 61/071,251, filed Apr. 18, 2008, Wondka et al., Expired.
U.S. Appl. No. 61/071,252, filed Apr. 18, 2008, Wondka et al., Expired.
U.S. Appl. No. 61/091,198, filed Aug. 22, 2008, Allum et al., Expired.
U.S. Appl. No. 61/101,826, filed Oct. 1, 2008, Wondka et al., Expired.
U.S. Appl. No. 61/106,414, filed Oct. 17, 2008, Wondka, Expired.
U.S. Appl. No. 61/136,269, filed Aug. 22, 2008, Allum et al., Expired.
U.S. Appl. No. 61/166,150, filed Apr. 2, 2009, Allum et al., Expired.
U.S. Appl. No. 61/239,728, filed Sep. 3, 2009, Cipollone, Expired.
U.S. Appl. No. 61/255,760, filed Oct. 28, 2009, Cipollone et al., Expired.
U.S. Appl. No. 61/294,363, filed Jan. 12, 2010, Allum et al., Expired.
U.S. Appl. No. 61/306,370, filed Feb. 19, 2010, Wondka et al., Expired.
U.S. Appl. No. 61/374,126, filed Aug. 16, 2010, Wondka et al., Expired.
U.S. Appl. No. 61/388,528, filed Sep. 30, 2010, Wondka et al., Expired.
U.S. Appl. No. 61/438,112, filed Jan. 31, 2011, Allum et al., Pending.
In the U.S. Patent and Trademark Office, Supplemental Notice of Allowance dated in re: U.S. Appl. No. 10/771,803, dated Dec. 2, 2008, 2 pages.
In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiners Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiners Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiners Interview Summary in re: U.S. Appl. No. 11/523,519, dated Jan. 16, 2009, 10 pages.
In the U.S. Patent and Trademark Office, Examiners Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiners Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiners Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiners Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.

(56) References Cited

OTHER PUBLICATIONS

Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "Adam Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.

Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
MacInryre et al., "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polokey et al., "Inspiratory pressure support reduces slowing of inspiratory muscle relations rate during exhaustive treadmill walking in sever COPD,"*Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.).
Rothfleisch et al., "Facilitation of fiberoptic nasotracheal intubation in a morbidly obese patient by simultaneous use of nasal CPAP," Chest, 1994, 106(1): 287-288.

(56) References Cited

OTHER PUBLICATIONS

Sanders et al., "CPAP Via Nasal Mask: A Treatment for Occlusive Sleep Apnea," *Chest*, 1983: 83(1), pp. 144-145.
Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.
Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," *Chest*, 1990: 97, pp. 364-368.
Tsuboi et al., "Ventilatory Support During Exercise in Patients With Pulmonary Tuberculosis Sequelae," *Chest*, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," *Cochrane Database Syst. Rev.*, 2002, 3: 1-22.
Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker' Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report dated Oct. 19, 2007 in co-pending EP 04762494.
International Search Report and Written Opinion for PCT/US04/26800 dated Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 dated Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.
Supplementary European Search Report, Application No. EP 10 81 4608, dated Aug. 25, 2014, 1 Page.
International Search Report and Written Opinion for Application No. EP 10 81 4608, dated Aug. 25, 2014, 6 Pages.
Masayuki Kanemaru, Notice of the Reason for Refusal, dated Jul. 31, 2014, 3 pages.
Espacenet, English Abstract JP2009160403, 2 Pages.
Espacenet, English Abstract JP2007518451, 2 Pages.
Chinese Office Action, No. 100140, dated Apr. 14, 2014, 14 Pages.
English Traslation Chinese Office Action, Application No. 201080049144, 27 Pages, dated Apr. 14, 2014.
Abstract CN1455690, Randall S. Hickle, Nov. 12, 2003, 2 Pages.
Abstract CN101365508, Steve Han, Feb. 11, 2009, 2 Pages.
Abstract CN1905917, Anthony Wondka, Jan. 31, 2007, 2 Pages.
English Translation of the First Office Action, Application No. 201080049144.6, pp. 1-13, Chinese Office Action, pp. 14-27, dated Apr. 4, 2014.
Office Action issued by SIPO in relation to Chinese Patent Application No. 2010800491446.
Chinese Office Action for Chinese Patent Application No. CN201080049144.6; dated Nov. 30, 2015.
Extended European Search Report, dated Aug. 31, 2015.
"Decision of Rejection" issued for Chinese Patent Application Serial No. 2010800491446 dated Jul. 29, 2016.
Notification of Reexamination for Chinese Patent Application No. 2010/80049144.6; dated Sep. 21, 2017.
Notification of Reexamination for Chinese Patent Application No. 2010/80049144.6; dated May 17, 2017.

\* cited by examiner

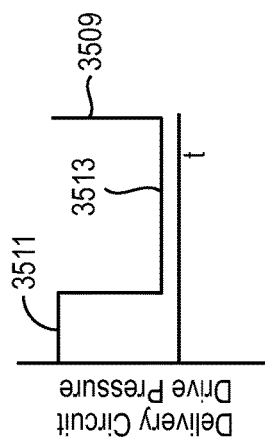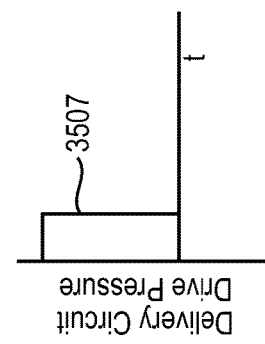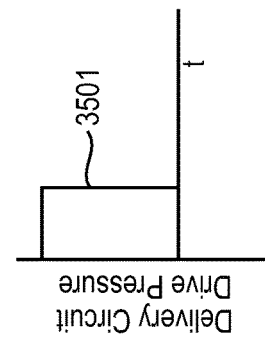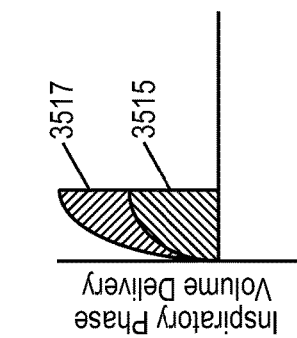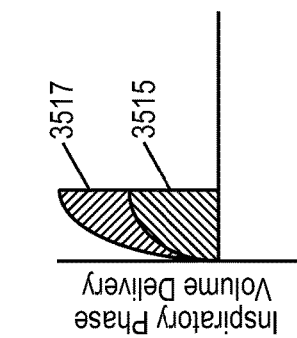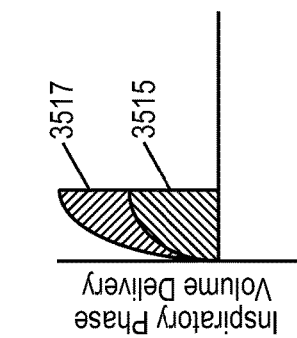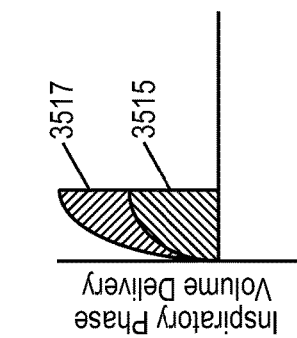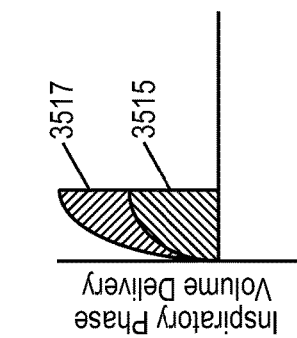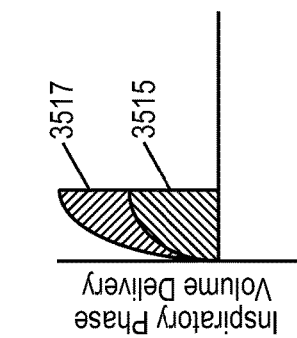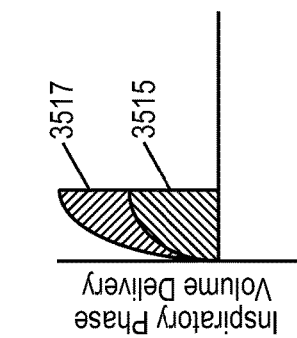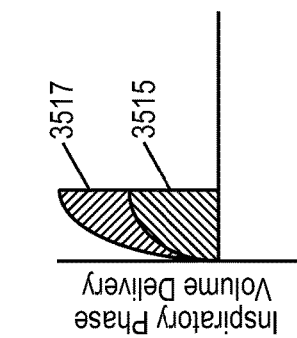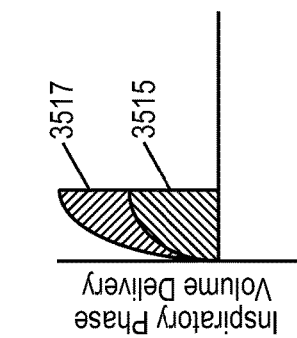

METHODS, SYSTEMS AND DEVICES FOR NON-INVASIVE VENTILATION INCLUDING A NON-SEALING VENTILATION INTERFACE WITH A FREE SPACE NOZZLE FEATURE

CROSS-REFERENCE TO RELATED APPLICATIONS

This application claims priority to U.S. Provisional Patent Application No. 61/239,728, filed Sep. 3, 2009, U.S. Provisional Patent Application No. 61/166,150, filed Apr. 2, 2009, U.S. Provisional Patent Application No. 61/255,760, filed Oct. 28, 2009, U.S. Provisional Patent Application No. 61/294,363, filed Jan. 12, 2010, and U.S. Provisional Patent Application No. 61/306,370, filed Feb. 19, 2010; the contents of which are incorporated by reference herein in their entireties. This application is also a continuation-in-part of each of U.S. Non-Provisional patent application Ser. No. 12/753,846, filed Apr. 2, 2010, PCT Patent Application No. PCT/US2010/029871, filed Apr. 2, 2010, U.S. Non-Provisional patent application Ser. No. 12/753,851, filed Apr. 2, 2010, PCT Patent Application No. PCT/US2010/029873, filed Apr. 2, 2010, U.S. Non-Provisional patent application Ser. No. 12/753,853, filed Apr. 2, 2010, U.S. Non-Provisional patent application Ser. No. 12/753,854, filed Apr. 2, 2010, PCT Patent Application No. PCT/US2010/029874, filed Apr. 2, 2010, U.S. Non-Provisional patent application Ser. No. 12/753,856, filed Apr. 2, 2010, and PCT Patent Application No. PCT/US2010/029875, filed Apr. 2, 2010; the contents of which are incorporated by reference herein in their entireties. This application incorporates by reference U.S. Non-Provisional patent application Ser. No. 12/876,098, filed Sep. 3, 2010, entitled "METHODS, SYSTEMS AND DEVICES FOR NON-INVASIVE VENTILATION INCLUDING A NON-SEALING VENTILATION INTERFACE WITH AN ENTRAINMENT PORT AND/OR PRESSURE FEATURE", and PCT Patent Application No. PCT/US2010/047921, filed Sep. 3, 2010, entitled "METHODS, SYSTEMS AND DEVICES FOR NON-INVASIVE VENTILATION INCLUDING A NON-SEALING VENTILATION INTERFACE WITH AN ENTRAINMENT PORT AND/OR PRESSURE FEATURE".

FIELD OF THE INVENTION

The present invention relates to the field of ventilation therapy for persons suffering from respiratory and breathing disorders, such as respiratory insufficiency and sleep apnea. More specifically, the present invention relates to providing open airway ventilation with methods and devices that use non-sealing non-invasive nasal ventilation patient interfaces.

BACKGROUND OF INVENTION

There is a need for a minimally obtrusive nasal mask and ventilation system that delivers mechanical ventilatory support or positive airway pressure, and which unencumbers the patient. There are a range of clinical syndromes that require ventilation therapy that would benefit from such a mask and system, such as respiratory insufficiency, airway or sleeping disorders, congestive heart failure, neuromuscular disease, and a range of situations that would be benefited, such as chronic, acute, emergency, mass casualty and pandemic situations.

Oxygen therapy is available with devices that do not encumber the patient. However, oxygen therapy is used for far less severe forms of clinical syndromes compared to ventilation therapy. For example, some nasal mask oxygen therapy systems have been developed for the purpose of delivering mixtures of air and oxygen by entraining air into the mask, however these are not considered ventilation therapy or respiratory support, because they do not mechanically help in the work of breathing. Recently, a variant of oxygen therapy has been employed, known as high flow oxygen therapy (HFOT). In this case, the oxygen flow rate is increased beyond standard long term oxygen therapy (LTOT), for example, above 15 LPM. Because of the high flow rate, the oxygen must be humidified to prevent drying out the patient's airway. It has been reported that HFOT can slightly reduce the patient's absolute pleural pressure during spontaneous breathing, thus have a slight effect on work of breathing. These systems are inefficient in that they consume a significant quantity of oxygen, rendering them non-mobile systems and encumbering the patient.

Respiratory support and ventilation therapies exist that provide mechanical ventilation (MV) to the patient, and mechanically contribute to the work of breathing. MV therapies connect to the patient by intubating the patient with a cuffed or uncuffed tracheal tube, or a sealing face or nasal mask or sealing nasal cannula. While helpful in supporting the work of breathing, the patient interfaces used for MV are obtrusive and/or invasive to the user, and MV does not facilitate mobility or activities of daily living, therefore encumbers that patient and is a drawback to many potential users. Non-invasive ventilation (NIV) exists which ventilates a patient with a face or nasal mask rather than requiring intubation, which can be an advantage in many situations. However, the patient cannot use their upper airway because the interface makes an external seal against the nose and/or mouth, and in addition the system is not mobile, the combination of which does not enable activities of daily living.

For treating obstructive sleep apnea (OSA), the gold standard ventilation therapy is continuous positive airway pressure (CPAP) or bilevel positive airway pressure (Bi-PAP), which is a variant to NIV in that the patient partially exhales through exhaust ports in the mask and back into large gas delivery tubing, rather than through an exhalation circuit as in MV. Continuous positive pressure applied by the ventilator to the patient by a nasal or face mask that seals against the nose or face prevents upper airway obstruction. While effective, this therapy has poor patient compliance because the patient interface is obtrusive to the patient and the patient unnaturally breathes through both a mask and gas delivery circuit.

In summary, existing therapies and prior art have the following disadvantages: they do not offer respiratory support or airway support in a manner that unencumbers the patient and (1) is non-invasive, and un-obtrusive such that it allows for mobility and activities of daily living, (2) allows the sensation of breathing from the ambient surroundings normally, and (3) is provided in an easily portable system or a system that can be easily borne or worn by the patient.

SUMMARY OF INVENTION

The invention provides ventilation to a patient using non-invasive open-airway ventilation (NIOV), and a non-sealing nasal mask interface with nozzles in free space that does not completely cover or seal the opening of the patient's mouth or nose.

Embodiments of the present invention may include a system for supplying ventilatory support, the system including a gas delivery source; a gas delivery circuit; a nasal interface configured to communicate with a patient's nose while allowing the patient to breathe ambient air directly without flowing through the nasal interface; a nozzle associated with the nasal interface at a distance from a nose, wherein the nozzle is connectable to the gas delivery circuit and the gas delivery source; and wherein the nozzle is capable of delivering gas into the nasal passage by creating negative pressure area near the nozzle and a positive pressure area near the entrance to the nose, wherein a combination of gas from the gas delivery source and air entrained from the gas exiting the nozzle provide ventilatory support.

Embodiments of the present invention may include a method for providing ventilatory support, the method including: providing a nasal interface that allows the patient to breathe ambient air through the nasal interface; providing a nozzle in free space associated with a proximal end of the nasal interface at a distance from a nose; adapting the nozzle to be in fluid communication with a gas delivery circuit and a gas delivery source, wherein the nozzle is capable of delivering gas into the nasal interface to create a negative pressure area near the nozzle and a positive pressure area near the entrance to the nose, and wherein a combination of gas from the gas delivery source and air entrained by the nozzle provides ventilatory support.

Certain embodiments of the systems and methods may also include that the positive pressure area may be created at a point outside the nose and distal to that point. The positive pressure area may be created at an edge of a nostril rim and distal to the edge. The positive pressure area may be created at a point in a nostril airway and distal to that point. The nasal interface may include a manifold, and wherein the manifold comprises the nozzle. The manifold may be configured to position the nozzle at a distance away from a nostril entrance, and may be configured to position the nozzle at an angle relative a centerline of a nostril airway. Embodiments of the present invention may include one or more sensors, wherein the one or more sensors comprise a sensing channel that extends away from the nozzle toward the nose terminating in the positive pressure area, and/or wherein the one or more sensors comprise a sensing channel that extends toward distally away from the nozzle. The sensing channel may extend into a nose. The sensing channel may extend to within approximately +/−5 mm from a nostril entrance. Embodiments of the present invention may include two or more nozzles per nostril. The nozzle may be an oval-shaped gas delivery nozzle orifice. The nozzle may include an array of multiple gas delivery nozzles arranged in a circular or oval pattern. Embodiments of the present invention may include a jet pump throat including a flow path. The jet pump throat may be associated with a manifold, and the nozzle may be associated with a jet pump throat flow path through the jet pump throat. The manifold may include an entrainment port in communication with the jet pump throat flow path. The nozzle may angle inward. The nozzle may angle inward at an angle of approximately 1-20 degrees. The nozzle may create an oval shaped gas delivery flow profile within a nostril airway. The nozzle may be rotatably adjustable. The nozzle may include at least one left nozzle and at least one right nozzle, wherein the spacing between the at least one left nozzle and the at least one right nozzle is adjustable. The at least one left nozzle and the at least one right nozzle may be rotate-ably adjustable. Spacing between a nostril entrance and nozzle may be adjustable. The nasal interface may be available in different sizes, differing in nozzle spacing, nozzle rotational orientation and nozzle distance to nostril entrance. The negative pressure area may extend from the nozzle to a location proximal to an entrance to a nose. A negative pressure may be less than ambient. The negative pressure may be approximately −5 to −28 cmH2O. The positive pressure area may extend from a location distal to the nozzle to an entrance to a nose. The positive pressure may be greater than ambient. The positive pressure may be approximately 0.01-0.50 psi. The combination of gas from the gas delivery source and the air entrained through entrained from the gas exiting the nozzle may be laminar flow within a nose. The nozzle may be positioned approximately 0-1.5 inches outside the entrance to the nose. Delivery of gas through the nozzle may be synchronized with a breathing pattern of a patient. The gas from the gas delivery source may be controlled by a wearable ventilator. Ventilatory support may include reducing the work of breathing to treat respiratory insufficiency. Ventilatory support may include elevating airway pressure to treat sleep apnea. The nasal interface may include a connector for coupling the system to a bridge of the nose and aligning the at least one gas delivery jet nozzle with the entrance of the nose. The connector may include a ledge to position the nasal interface relative to an edge of a nostril rim. The connector may adjust the angle of the nozzle to be in alignment with a centerline of a nostril airway.

Embodiments of the present invention may include a system for supplying ventilatory support, the system including: a gas delivery source; a gas delivery circuit; a nasal interface configured to communicate with a patient's nose while allowing the patient to breathe ambient air directly without flowing through the nasal interface; a nozzle associated with the nasal interface at a distance from a nose, wherein the nozzle is connectable to the gas delivery circuit and the gas delivery source; a jet pump throat comprising a flow path through the jet pump throat, wherein the jet pump throat is associated with a manifold, and the nozzle is associated with a jet pump throat flow path through the jet pump throat; and an entrainment port in communication with the jet pump throat flow path, wherein the nozzle is capable of delivering gas into the nasal passage by creating negative pressure area near the nozzle within the jet pump throat flow path and a positive pressure area within the jet pump throat flow path distal to the nozzle, wherein a combination of gas from the gas delivery source and air entrained through the entrainment port provide ventilatory support. Certain embodiments of the systems and methods may include that ventilatory support includes reducing the work of breathing to treat respiratory insufficiency. Ventilatory support may include elevating airway pressure to treat sleep apnea.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention.

FIG. 30A graphically shows a square waveform gas delivery pressure, according to one embodiment.

FIG. 30B graphically shows the volume delivery of FIG. 30A.

FIG. 30C graphically shows resulting lung pressure of FIG. 30A.

FIG. 30D graphically shows a sinusoidal waveform gas delivery pressure, according to one embodiment.

FIG. 30E graphically shows the volume delivery of FIG. 30D.

FIG. 30F graphically shows resulting lung pressure of FIG. 30D.

FIG. 30G graphically shows a square waveform gas delivery pressure for a portion of the inspiratory phase, according to one embodiment.

FIG. 30H graphically shows the volume delivery of FIG. 30G.

FIG. 30I graphically shows resulting lung pressure of FIG. 30G.

FIG. 30J graphically shows a multi-level waveform gas delivery pressure, according to one embodiment.

FIG. 30K graphically shows the volume delivery of FIG. 30J.

FIG. 30L graphically shows resulting lung pressure of FIG. 30J.

DETAILED DESCRIPTION OF THE EMBODIMENTS

Figure 1:
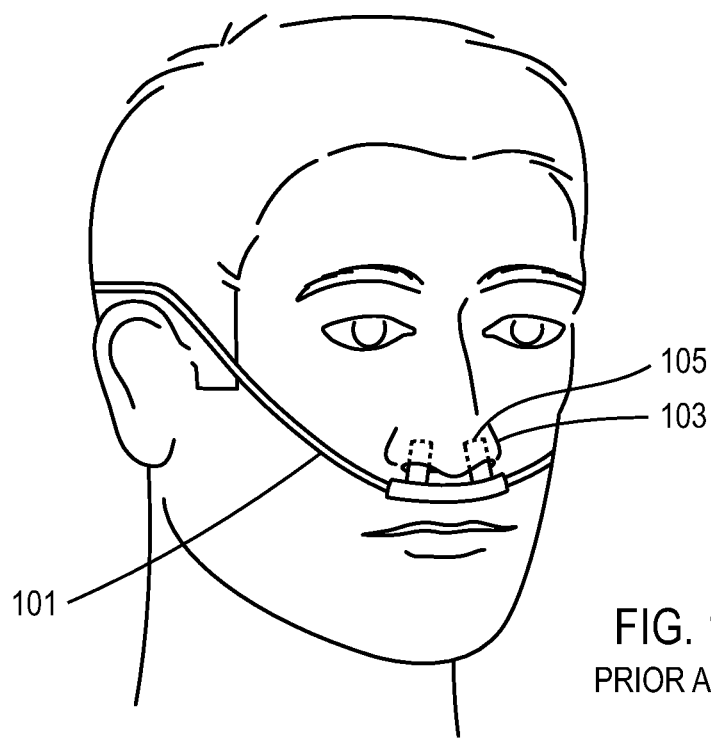
FIG. 1 shows a prior art conventional oxygen delivery cannula for administering oxygen therapy.

FIG. 1 shows a prior art conventional oxygen delivery cannula 101 for administering oxygen therapy. Extensions 105 on the cannula 101 are configured to enter nares 103. A proximal end (not shown) of the cannula 101 is connected to an oxygen delivery device that delivers continuous flow oxygen at 1-6 LPM to the user's nose, or delivers a bolus of oxygen upon detection of an inspiratory effort. The system of FIG. 1 does not mechanically support the work of breathing of the patient, and is not believed to be effective in preventing moderate to severe forms of OSA. The cannula of FIG. 1 is also used with another oxygen delivery therapy, high flow oxygen therapy (HFOT), in which more than 15 LPM of humidified oxygen is delivered at a continuous flow rate to the user's nose. Due to the high flow required for HFOT, the system is non-portable and the oxygen must be humidified.

Figure 2:
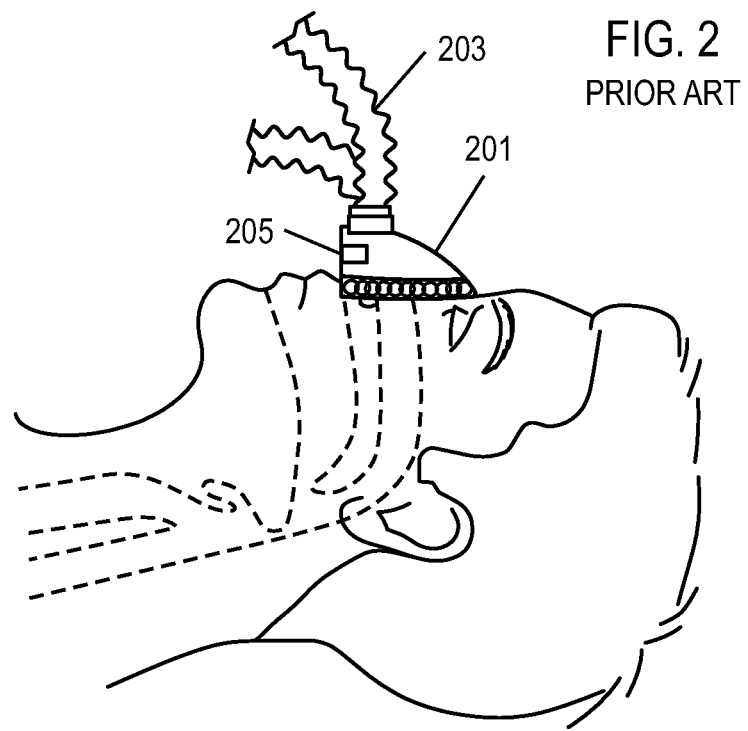
FIG. 2 shows a prior art conventional non-invasive ventilation using a nose mask and using a CPAP or BiPAP ventilation mode.

FIG. 2 shows a prior art respiratory support therapy for non-invasive ventilation (NIV), using a nose mask 201 in a bilevel positive airway pressure (BiPAP) ventilation mode. NIV is used to breathe for the patient, or can be used to help the breathing of a patient, in which case the patient's spontaneous breathing effort triggers the ventilator to deliver the pressure or volume-based mechanical ventilation (MV). All of the volume delivered to and from the lungs is delivered and removed from a ventilation circuit 203 and the nose mask 201.

A similar system to FIG. 2 can be used for OSA where a mask is sealed to the face so ventilation gas is provided by the ventilator and a portion of exhaled gas is exhaled through exhaust vents 205. NIV, continuous positive airway pressure (CPAP) and BiPAP are believed to be clinically effective modes and therapies for spontaneously breathing patients. These modes and therapies, however, do not facilitate activities of daily living (ADL's). For example, the ventilator cannot be borne by the patient, the patient cannot breathe room air naturally and freely because of the sealing mask, and the patient's upper airway cannot function normally and naturally because it is sealed off with the external mask seal, and in addition the gas delivery tubing is too bulky to realistically support mobility and ADL's.

Embodiments of the present invention will now be described with reference to the remaining figures. Respiratory support or airway support is provided in a manner and way that the patient is unencumbered. The non-invasive, non-sealing and unobtrusive systems and methods may allow for mobility and activities of daily life. The systems and methods allow for the sensation of breathing from ambient surroundings normally. The systems and methods provide an easily portable system that can be readily borne or worn by the patient, and gas delivery tubing that does not encumber the patient.

Systems and methods may include a gas delivery source, a gas delivery circuit, and a nasal interface that allow breathing ambient air through the nasal interface. A gas flow path through the nasal interface may have a distal gas flow path opening. A nozzle may be associated with a proximal end of the nasal interface a distance from the distal end gas flow path opening. In certain embodiments, at least a portion of an entrainment port may be between the nozzle and the distal end gas flow opening. The nozzle may deliver gas into the nasal interface to create a negative pressure area in the gas flow path at the entrainment port. The nasal interface and the nozzle may create a positive pressure area between the entrainment port and the distal end of the nasal interface. Gas from the gas delivery source and air entrained through the entrainment port may increase airway pressure.

Figure 3:
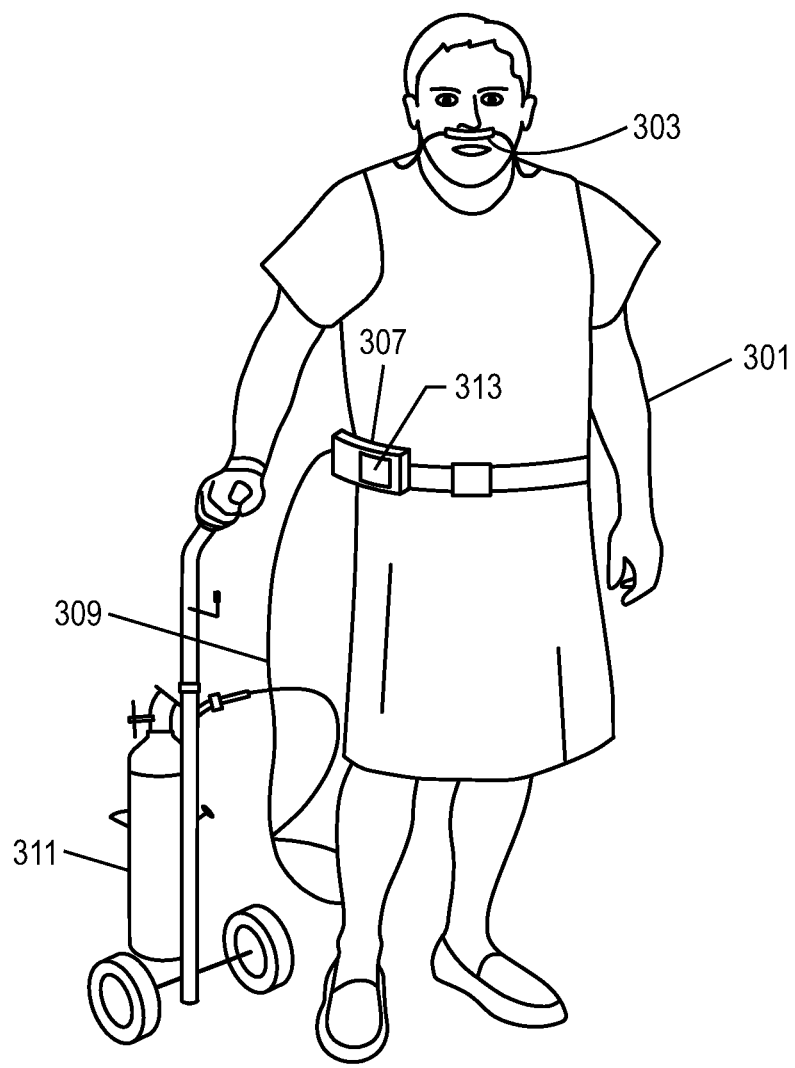
FIG. 3 shows an unencumbered patient using an embodiment of the invention to receive work of breathing support while ambulating.

FIG. 3 shows a patient 301 using an embodiment of the invention to provide mechanical ventilatory support, or work of breathing support, while being mobile. Conventional ventilators would require the patient to be stationary while receiving ventilatory support, or to use a wheel chair to carry the bulky and heavy equipment that is required for conventional ventilators. Conventional ventilators also require an encumbering sealing mask and large bore gas delivery tubing. The patient may also wear a ventilator module 307, which may be ultra-small that enables mobility when the invention is used for respiratory insufficiency. The ventilator may be coupled by tubing or other means 309 to an air and or oxygen supply 311. The ventilator module 307 may include a display 313 and/or input devices.

The present invention may include a non-sealing nasal mask patient interface, connected to the ventilator with small bore gas delivery tubing. The nasal mask may be uniquely non-sealing, so that the patient can inhale and exhale ambient air directly through the mask while receiving ventilatory support, in which there is negligible dead space volume in the mask. The mask may include a unique Venturi system that makes it possible for the ventilator to deliver relatively small amounts of gas to achieve relatively high levels of ventilatory support or airway pressure. The Venturi mask is described in more detail in FIGS. 6-31.

Various embodiments of the nasal interface 303 are described in detail in the following disclosure. The nasal interface 303 may be minimally obtrusive compared to standard masks, so that the patient can feel and act normally while receiving the therapy. For example, the patient can talk, swallow, eat or drink, and feel like they are breathing normally, with the nasal interface and therapy. The gas delivery tubing required may be very small compared to standard ventilator tubing, which more readily allows the patient to move around with the system, and to conceal the equipment and tubing needed for the therapy. The efficiency of the Venturi system in achieving therapeutic levels of lung or airway pressure while using low levels of gas volume, allows the gas supply to be relatively small, further enabling mobility of the patient, and or miniaturization of the ventilation equipment. A nasal interface may be configured to communicate with a patient's nose while allowing the patient to breathe ambient air directly without flowing through the nasal interface.

While FIG. 3 shows the patient using the invention for mobility, the invention can also be applied to sleep disordered breathing. In the later case, an advantage of the invention is that the mask and tubing is smaller than standard sleep apnea therapy masks and tubing. Additionally, the patient can have the sensation of breathing ambient air more directly making the therapy tolerable to the patient, rather than breathing through a machine, which is the sensation when using standard sleep apnea ventilation devices.

Figure 4:
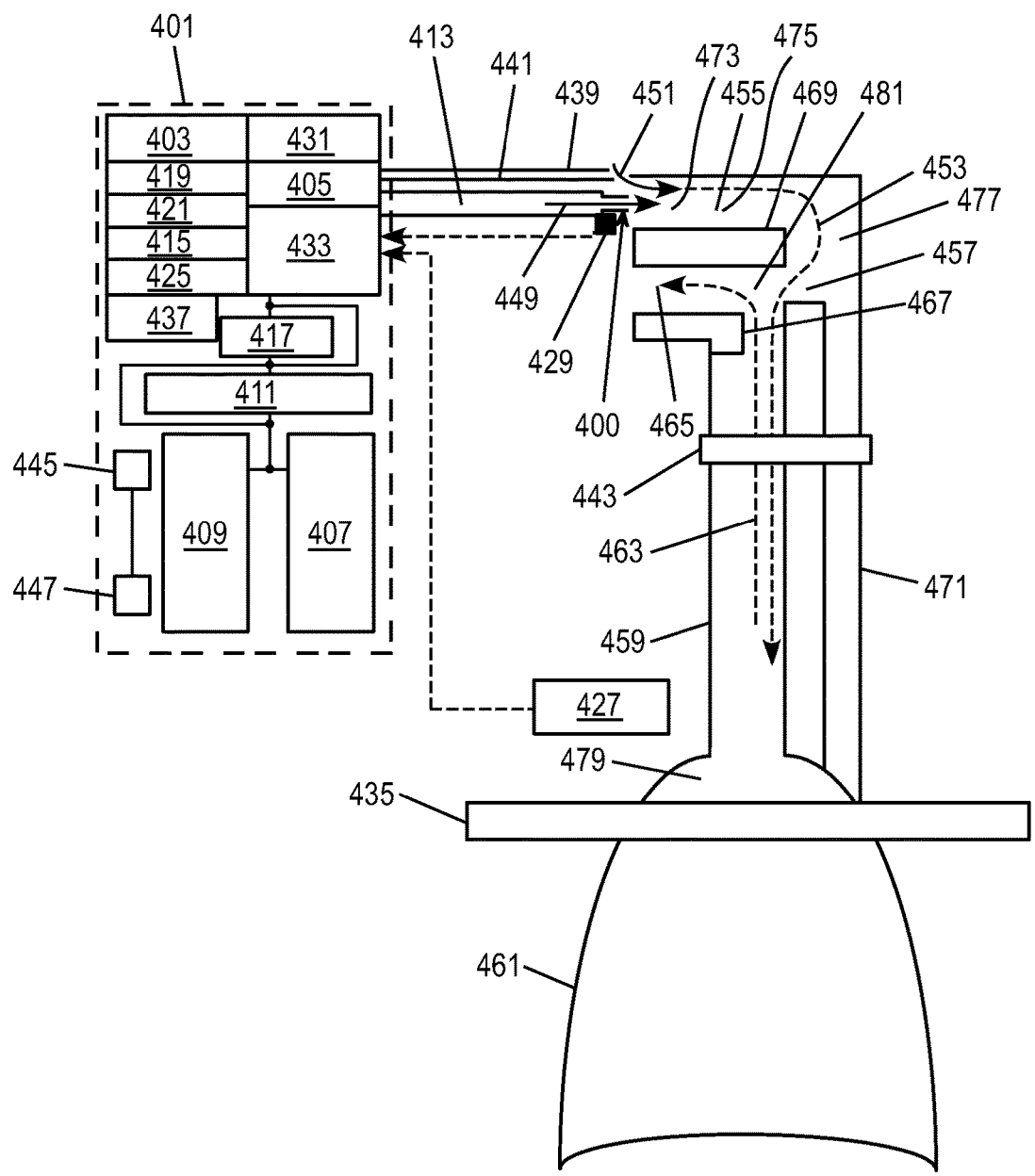
FIG. 4 is a schematic showing an exemplary system of the invention.

FIG. 4 is a block diagram describing an exemplary system of the invention. The exemplary system of FIG. 4 may be a wearable ventilator with portable gas source as shown in FIG. 3, or may be a different ventilator and/or gas source. Ventilator and patient interface features associated with the system are shown schematically. FIG. 4 depicts a non-invasive open nasal interface 400. The non-invasive open nasal interface will be described in various embodiments described herein, for example, in FIGS. 5-8B (curved nasal mask), FIGS. 9-15 (flexible joint), and FIGS. 16-25 and 29-31 (ergonomic configuration).

A ventilator module 401 may include or is in communication with several other functional accessories. The ventilator and the patient's internal anatomy from FIG. 3 are shown in schematic format in FIG. 4. A nasal airway pressure sensor 429 is typically included. A transmitter 403 may be included to transmit information regarding the patient, the patient's therapy, and the ventilator performance to a remote location for review, analysis, remote intervention, two-way communication, and archiving. For example, the patient's compliance with the therapy or utilization of the therapy can be monitored and assessed. Important information can be trended, for example the patient's breath rate, I:E ratio, oxygen usage, activity level, or depth of breathing. Also, information can be sent to a ventilator 433, such as for example, sending programming instructions for setting titration options for the ventilator output to meet the needs of the patient, or sending instructions to the patient. The patient can also send information or questions to a remote clinician through the ventilator and transmitter 403.

An oxygen source 407 and/or a compressed air source 409 can be included, typically external to the ventilator module 401. In certain embodiments, however, the oxygen source 407 and/or the compressed air source 409 can be internal to the ventilator module 401 if the therapy is being used for stationary use, for example, in the home. A blender 411 can be included to control the fractional delivered O2 in a gas delivery circuit 413. A pulse oximeter 415 can be used to titrate settings of the ventilator module 401 to meet the physiological needs of the patient, for example setting the correct oxygen blender setting or ventilator volume output. In addition to compressed supplies of oxygen and air gas, the ventilator module 401 can include internal or external air and oxygen generating systems 417, such as a compressor, pump or blower to create pressurized air, an oxygen generator and/or pump to create pressurized oxygen gas, and/or a compressed gas accumulator. The oxygen source can also be liquid oxygen, or a liquid oxygen generating system. An internal or external humidifier 405 can be included for extended uses of the therapy, or if using in dry climates.

As the therapy is frequently used to help ADL's, and to promote activity, a pedometer 419 and/or actigraphy sensor 421 can be included internal to or external to a ventilator module 401. Optional sensors may include a $CO_2$ sensor 425, and/or an external breathing sensor unit 437. A $CO_2$ sensing line 439 and/or an airway pressure sensing line 441 may be present. One or more other external sensors may be included. For example, other external sensors may include an external respiration sensor or respiration effort sensor 427, such as a respiratory muscle effort sensor, a chest impedance sensor 435, or other types of sensors, such as a tracheal or other microphone or vibration sensor 443 or acoustical or ultrasonic sensor. The one or more external sensors may be used either as a redundant sensor to a nasal airflow or nasal pressure sensor 429, or to complement the information obtained from the nasal airflow or nasal pressure sensor 429, or in place of the nasal airflow or nasal pressure sensor 429. An oral airflow breathing sensor may also be used, for example nasal airflow or nasal pressure sensor 429 may alternatively be an oral airflow sensor.

A drug delivery module 431 can be incorporated internally or externally to a ventilator module 401. Because of the challenges with current aerosolized drug delivery inhalers, the drug delivery module 431 can be used to propel and deposit medication particles deep in the respiratory system without a carrier propellant. Because the patient's using the therapy often may also require prescription medication, this may be a convenient and efficient way to administer the medication.

When the therapy is being used for respiratory support, the user may have two options: (1) wearing or toting the ventilator module 401 so that the user can be ambulatory or enjoy the activities of daily living, or (2) stationary use, in the event the patient plans on being stationary or does not have the ability to ambulate. For the later, the delivery circuit can optionally be provided in a 25-100 foot length, such that the gas source and ventilator module 401 can be stationary in the patient's home, while the patient can move around their home while wearing the interface and receiving the therapy. Or, the gas source can be stationary, and connected to the ventilator module 401 with a 25-100 foot hose, so that the patient can wear or tote the ventilator and be mobile within the range of the hose.

The ventilator module 401 may include one or more processors 445 and one or more memories 447 to analyze information and output therapies.

Ventilation gas 449 may exit at a speed that entrains ambient air 451, such that the combination of ventilation gas 449, entrained ambient air 451 and spontaneously inhaled air, if the patient is spontaneously breathing, is delivered 453 to the patient's airways, such as the nasal cavity 455, oropharyngeal airway 457, trachea 459, lung 461 and others, under power to create a clinically efficacious effect on the lung and airways. Patient may exhale 463 through the nose or mouth. Various airways are also included, such as nostril airway 473, nasal airway 475, oral airway 481, upper airway 477, and lower airway 479.

When using the invention, the patient breathes normally through their upper airway and through their nose, while receiving mechanical support through the interface. During exhalation, the exhaled gas preferably does not enter the gas delivery circuit but rather exits the nose or mouth directly to ambient air, or through, across or around the nasal interface 400 to ambient air. The patient can keep their mouth closed during use for example during inspiration, to help direct the mechanical support to the lower airways and past the oral cavity 465, base of the tongue 467, palate 469 and esophagus 471, or can use a mouth guard or chin band, if necessary. The patient may exhale through their mouth when using the therapy.

FIGS. 5-26 describe embodiments of the non-sealing open-airway nasal mask with nozzles in free space. Systems and methods are described for ventilating a patient in a manner that unencumbers the user, by using a nasal ventilation patient interface and system that allows the user to breathe ambient air around the interface. A gas delivery nozzle may be associated with the nasal interface at a distance from a nose. The nozzle is connectable to a gas delivery circuit and ventilator, and delivers gas front the nasal interface toward the nose. The nasal interface and the nozzle create a negative pressure area near the nozzle, and a positive pressure area near the entrance to the nose. A combination of gas from the ventilator and entrained air are delivered to the patient to support the work of breathing.

Figure 5:
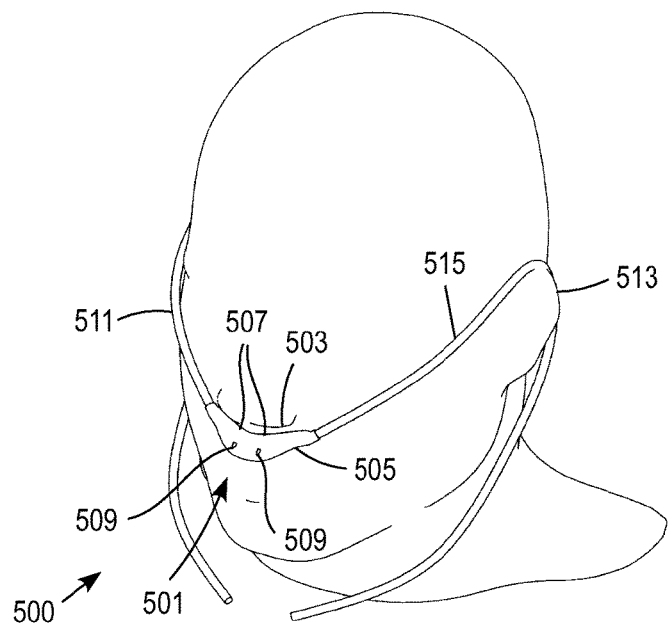
FIG. 5 shows an exemplary embodiment where an open non-sealing nasal ventilation mask is configured to be placed under the nose of the user, and which may extend bilaterally from the midline of the face to the sides of the nose.

FIG. 5 describes an embodiment of the invention, showing a ventilation nasal mask assembly 500 with a nasal mask 501 configured to be placed under a nose 503 of a user, without sealing or impeding ambient air from freely flowing in and out of the nose 503. The nasal mask 501 may include a manifold 505. The nasal mask 501 may also include one or more breathing pressure sensing ports 507 or sensors, which are positioned close to an entrance to the nares. The nasal mask 501 may include one or more gas delivery nozzles 509 spaced a distance away from the entrance to the nose 503. The one or more gas delivery nozzles 509 may direct ventilation gas into the nasal airway, and entrain ambient air into the nasal airway.

Gas delivery tubing 511 and pressure sensing tubing 515 from a ventilator, as shown in FIG. 4, may be coupled to the manifold 505 at proximal ends of the manifold 505. The gas delivery tubing 511 and pressure sensing tubing 515 may be routed bilaterally away from the manifold 505 and around ears 513 of the user.

Figure 6:
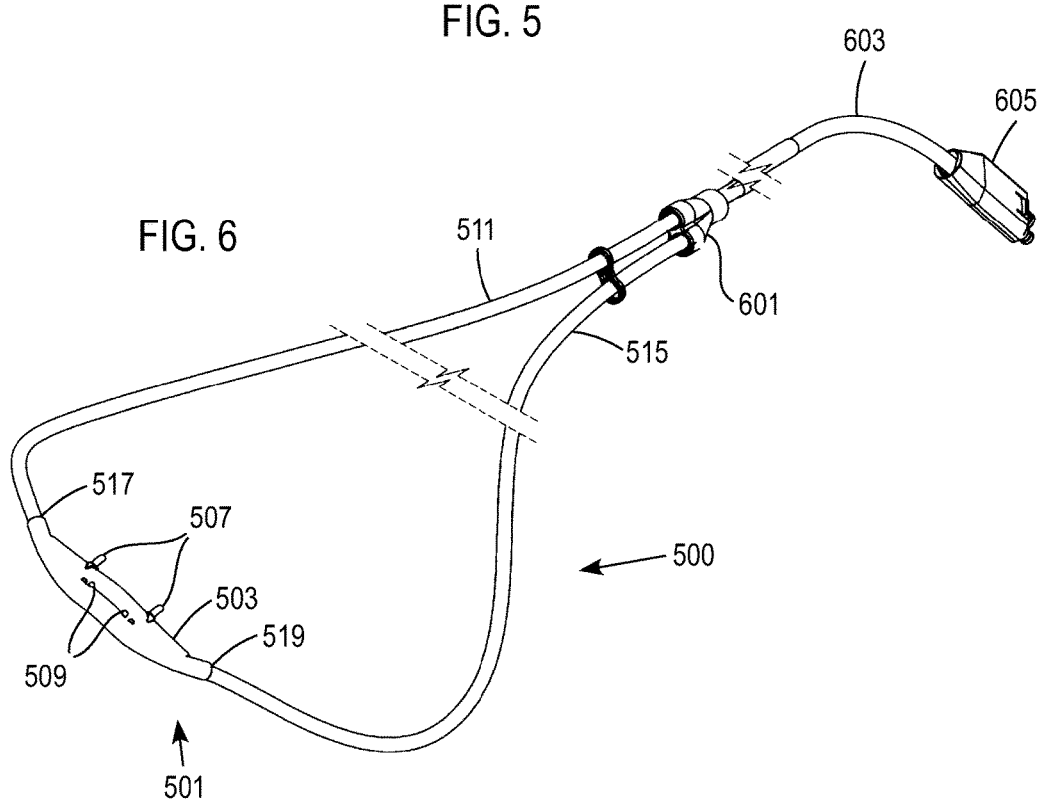
FIG. 6 is a perspective view of the nasal mask assembly of FIG. 5.

FIG. 6 shows an isometric view of the nasal mask assembly 500, including the nasal mask 501 at the distal end of the nasal mask assembly 500, gas delivery tubing 511 and pressure sensing tubing 515 attached to the manifold 505 at a distal end of the gas delivery tubing 511 and pressure sensing tubing 515, a Y connector 601 joining the gas delivery tubing 511 and pressure sensing tubing 515 at proximal ends of each arm of the gas delivery tubing 511 and pressure sensing tubing 515, and a combined gas delivery and pressure sensing tubing 603 extending from the Y connector 601 to a ventilator connector 605.

In certain embodiments, a rotatable joint 517 between the gas delivery tubing 511 and manifold 503 and/or a rotatable joint 519 between the pressure sensing tube 515 and manifold 503, may include detent settings. These detent setting joints 517, 519 can be used to adjust the angle of the manifold 503 to adjust the angle of the gas delivery nozzles 507 to be in alignment with the patient's nostril airway. Alternatively, the gas delivery tubing 511 and pressure sensing tubing 515 can be connectable to the manifold 503 in different rotational orientations to likewise align the gas delivery nozzles 507 with the patient's nostril airway.

Figure 7:
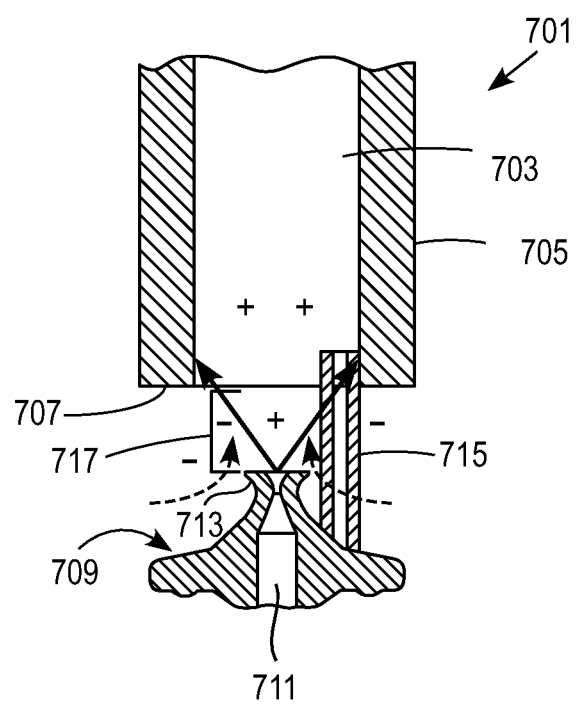
FIG. 7 shows a front view schematic illustration of an embodiment of the nasal mask.

FIG. 7 describes a front view cross-sectional schematic representation of a nasal mask 701, showing one exemplary side of the nasal mask 701, for example, the left side. FIG. 7 shows a nostril airway 703, a nostril wall 705, a nostril entrance 707, a gas delivery nozzle 713, a gas flow channel 711 through the gas delivery nozzle 713, a manifold 709 that integrates the gas delivery nozzle 713, a breathing pressure sensing cannula 715, and a distance 717 between the gas delivery nozzle 713 and the nostril entrance 707. A rounded distal tip of the gas delivery nozzle 713 may be used to assist in reduction of sound generated by gas exiting the gas delivery nozzle 713.

FIG. 7 shows a specific nozzle tip to illustrate that the nozzle tip might be flared or rounded for sound mitigation. The flare is an option.

Distance from Nozzle to Nose:

The gas delivery nozzle 713 may be integrated into a manifold 709, and the manifold 709 may be shaped, dimensioned and configured to position the gas delivery nozzle 713 at an ideal position under a nostril entrance 707. A distance of the gas delivery nozzle 713 to the nostril entrance 707 may be chosen to optimize the function of the Venturi created by the gas delivery nozzle 713 and the nares. Optimal function may be described as generating maximal pressure in the nostril airway 703 while the gas delivery is still comfortable and tolerable to the user.

Typically, laminar positive pressure flow should be developed before the airflow reaches deep into the nostril. This positive pressure flow may be defined by the area inside and distal to the gas flow cone defined by the gas exiting the gas delivery nozzle 713. The area outside of this cone is negative pressure created by the Venturi, which entrains ambient air into the nose and nasal passage, thus generating the energy required for mechanical ventilatory support. When this cone intersects with the internal wall of the nostril, the distal side of that intersecting point is positive pressure.

Alternatively, based on position of the gas delivery nozzle 713 and other operational parameters and device dimensions, this cone can be wider than the entrance to the nostril when it reaches the nostril. In this event, positive pressure occurs outside of the nostril and extends distally. Also alternatively, this cone can intersect with the nostril walls at a distance inside the nostril, thereby allowing a negative pressure zone to occur at the entrance to and slightly inside the nostril, but then transitioning to positive pressure distal to the intersecting point. Because the cross sectional geometry is non-uniform, for example, not a perfectly circular, there is variability with the gas flow cone intersecting points with the nostril wall, around the circumference of the cone and nostril. As will be described subsequently, specific embodiments of the nasal mask may address this nuance such that more uniform and predictable performance can be achieved.

In the embodiment of FIG. 7, the nostril entrance 707 may act as a jet pump inlet and the nasal passage may act as a jet pump throat. Intuitively, it would be expected that optimal function would dictate placing the gas delivery nozzle 713 at the nostril entrance 707 or slightly inside the nares; however, it was determined through empirical testing than in the average adult user, the optimal position for the gas delivery nozzle 713 to achieve optimal Venturi function is to place the gas delivery nozzle 713 approximately 0.950 inches from the nostril entrance 707.

Position of Breathing Pressure Sensing Port:

For embodiments of the invention to be effective, it may be necessary to measure and monitor breathing of the patient to properly synchronize a ventilator gas delivery control system with spontaneous breathing patterns of the patient, as desired clinically. Therefore, while the gas delivery nozzles 713 may be positioned ideally at a distance away from the user's nostril entrance 707, breathing pressure sensing cannula 715, breathing pressure sensing ports or other sensors may need to be placed near, at or inside the nostril entrance 707. For example, the distal end of the pressure sensing cannula 715 can be placed slightly inside the nose in the area where positive pressure has been created by the Venturi system.

It may be beneficial to have multiple locations for measuring pressure. For example, one location may be used for detecting and measuring the spontaneous breathing pressure of the patient, and a different location for measuring the pressure generated by the ventilation system. For example, a breathing pressure sensing port may be placed slightly inside the nostril entrance 707, and a ventilation gas pressure sensor may be placed outside the nostril entrance 707, or alternatively deeper inside the nostril airway 703.

The location of pressure sensing ports, such as the breathing pressure sensing cannula 715, may be selected to optimize accuracy and fidelity. For example, a breathing pressure sensing port, such as the breathing pressure sensing cannula 715, may be arranged so that it is located near the medial aspect of the nostril airway 703, or at the posterior aspect of the nostril airway 703. Multiple breathing pressure sensing locations may also be used. For example, a sensing port at a medial posterior aspect of the nostril airway 703 may be used to measure inhalation pressures accurately, and a sensing port at the anterior aspect of the nostril airway 703 may be used to measure exhalation pressures accurately.

In addition to a nostril airway breathing pressure sensor, other sensor types or locations may be used. For example, a microphone or ultrasonic sensor can be used to detect phases of breathing when placed on the user's neck to detect movements of air in the trachea. Other sensors and sensor locations can be used.

In addition to the ventilation pressure being measured by a pressure sensing port outside of the nose, at the nostril entrance, or inside the nostril airway, the ventilation pressure can be derived by other apparatus and methods. For example, a gas delivery pressure in the gas delivery circuit can be correlated to a delivered ventilation pressure that is delivered to the patient by the ventilation system by measuring key relevant patient parameters, such as airway resistance and respiratory track compliance, and correlating those parameters with delivered pressure based on a gas delivery pressure.

Figure 8:
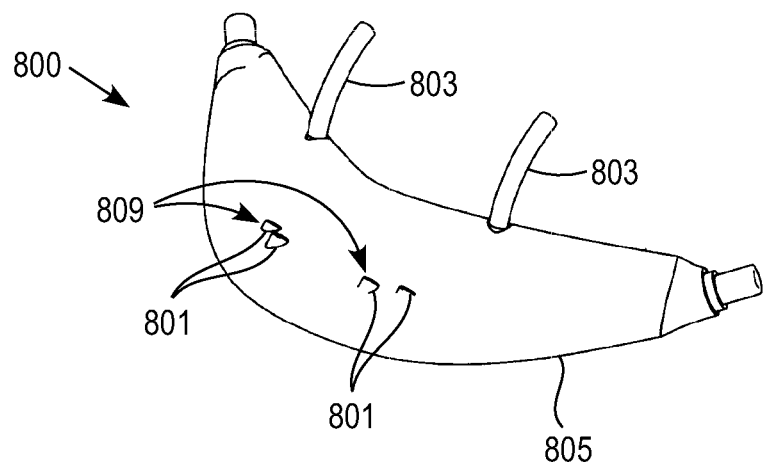
FIG. 8 shows an anterior-top-side view of the nasal mask of FIG. 5.

FIG. 8 shows a top-side view of the nasal mask 800 of an alternative embodiment of FIG. 5, showing gas delivery nozzles 809 and pressure sensing cannula 803. The gas delivery nozzles 809 may include a pair of exit ports 801 for both the right and left gas delivery nozzles 809. As discussed later, the dual exit ports 801 may improve the function and user tolerability of the device.

Figure 9:
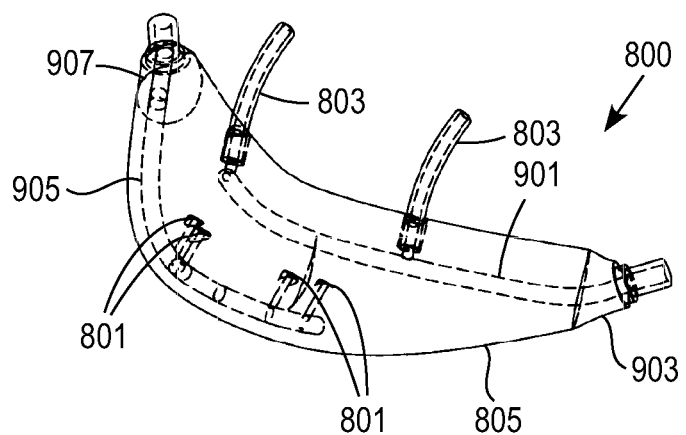
FIG. 9 shows a hidden line view of the nasal mask of FIG. 8, showing the gas flow path and breathing pressure sensing path.
Figure 10:
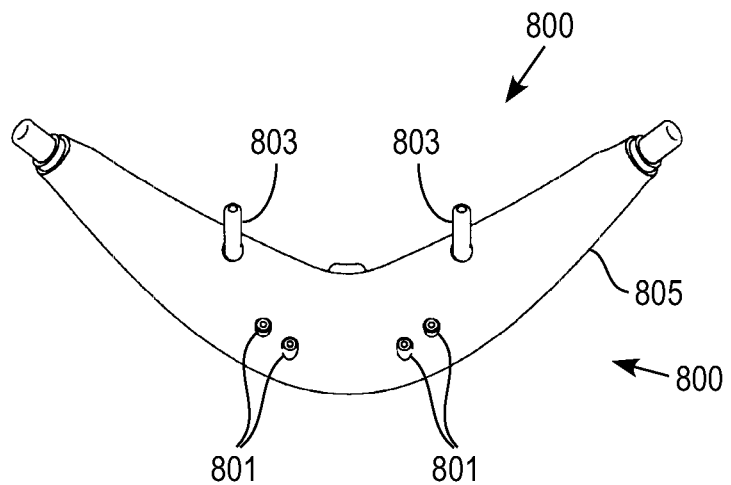
FIG. 10 shows a top view of the nasal mask of FIG. 5.
Figure 11:
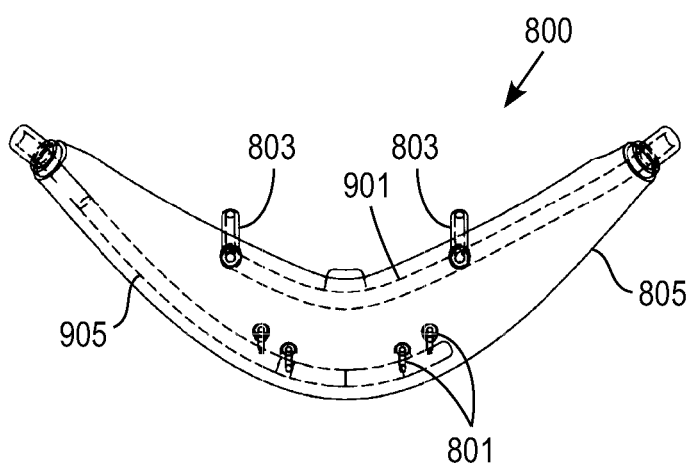
FIG. 11 shows a hidden line view of the nasal mask of FIG. 10, showing the gas flow path and breathing pressure sensing path.
Figure 12:
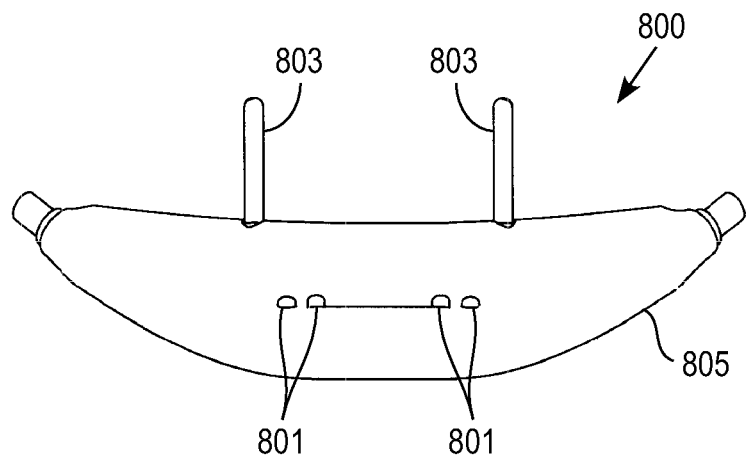
FIG. 12 shows a rear-top view of the nasal mask of FIG. 5.
Figure 13:
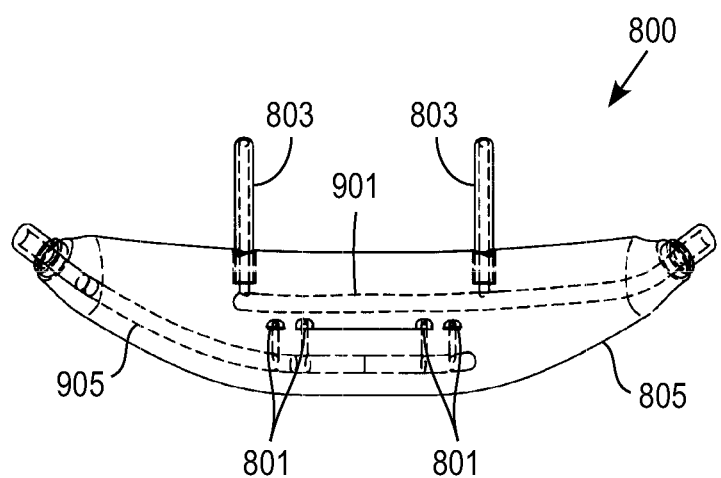
FIG. 13 shows a hidden line view of the nasal mask of FIG. 12, showing the gas flow path and breathing pressure sensing path.

FIG. 9 shows a hidden line view of the nasal mask 800 and manifold 805 shown in FIG. 8, including a pressure sensing lumen 901 running from a first proximal end 903 of the manifold 805 to and through each of the pressure sensing cannula 803, and a gas delivery lumen 905 running from a second proximal end 907 of the manifold 805 to and through each of the exit ports 801. FIG. 10 shows a top view of the nasal mask 800 shown in FIG. 8, and FIG. 11 shows a hidden line view of the nasal mask 800 shown in FIG. 10. FIG. 12 shows a front-top view of the nasal mask 800 shown in FIG. 8, and FIG. 13 shows a hidden line view of the nasal mask 800 shown in FIG. 12.

Key dimensions and values of the ventilation nasal mask are indicated in Table 1. The parameters provided by the ventilation nasal mask and system are indicated in Table 2. Additional exemplary dimensions, values and materials of the ventilation nasal mask are indicated in Table 3.

Nozzle Patterns:

In certain situations, delivery of ventilation gas to the patient through one left and one right gas delivery nozzles may not develop the laminar flow desired due to the variability found in patient's nostril and nasal air passage geometries. Therefore, in certain embodiments of the invention, the mask's left and right gas delivery may each be performed by multiple nozzles.

Figure 14:
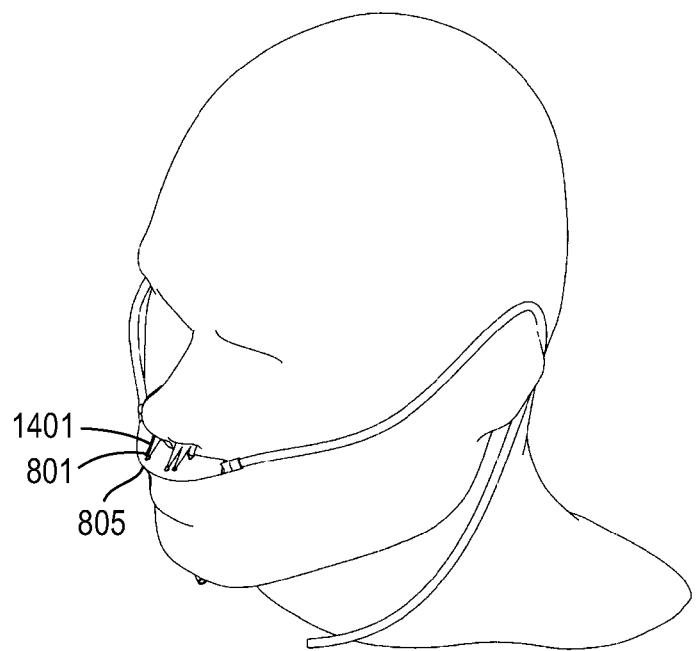
FIG. 14 shows a pattern created by flow emission from gas delivery nozzles.
Figure 15:
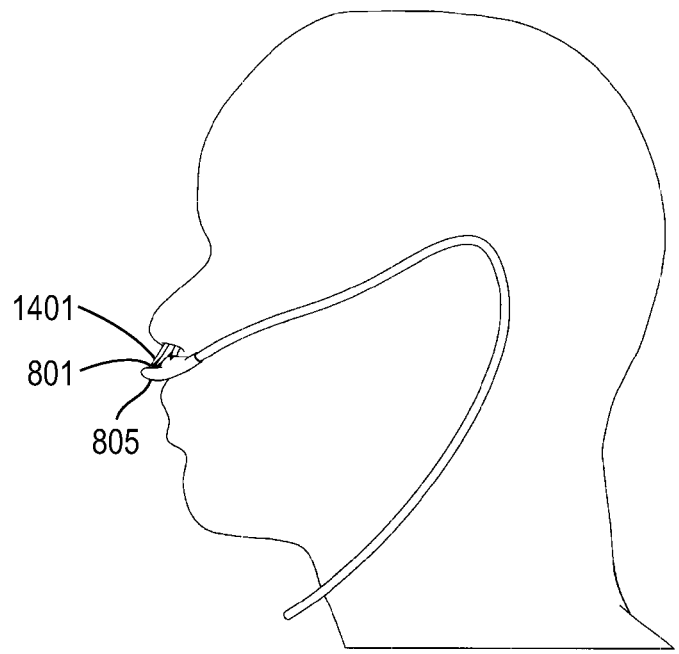
FIG. 15 shows a pattern created by flow emission from gas delivery nozzles.
Figure 16:
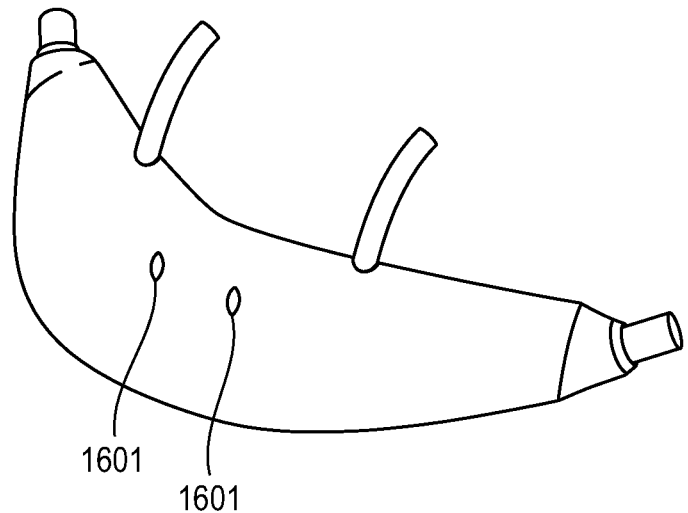
FIG. 16 shows an embodiment of the nasal mask shown in FIG. 5 with oval gas delivery nozzles.
Figure 17:
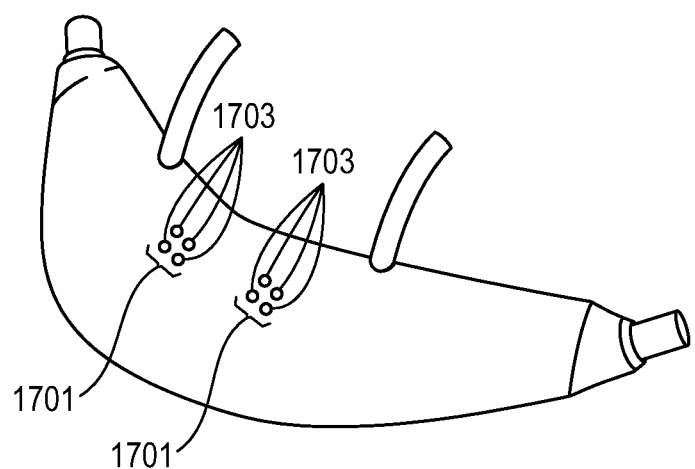
FIG. 17 shows an embodiment of the nasal mask shown in FIG. 5 with multiple gas delivery nozzles arranged in an anatomically functional pattern.

For example, as shown in FIG. 8, a pair of left and a pair of right gas exit ports 801 may be incorporated in the manifold 805, such that the pattern created by the gas exiting the exit ports 801 is spread out in a pattern approximating the cross-sectional area of the nostril airway, and thus facilitating creating laminar positive pressure flow. The pattern 1401 created by flow emission from the exit ports 801 is shown in FIGS. 14 and 15. This flow and pressure head profile spreads out and smoothes out the flow profile, which may optimize the flow characteristics, and facilitate creating laminar positive pressure flow with minimal disturbance and resistance. Other embodiments may also be used. For example, an oval shaped gas delivery nozzle orifice 1601, as shown in FIG. 16, or a gas delivery nozzle array 1701 of individual gas delivery nozzles 1703, for example arranged in a circular or oval pattern, as shown in FIG. 17. Any nozzle pattern may be used.

Figure 18:
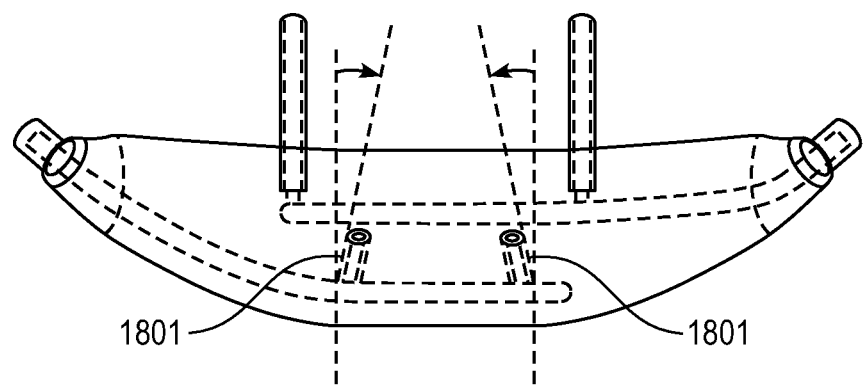
FIG. 18 shows a hidden line view of the mask view of an embodiment of the nasal mask, showing the gas flow path and breathing pressure sensing path, in which the gas delivery nozzles are angled inward toward the midline.

In addition to the gas delivery nozzle pattern, the included angle between the gas flow path axis created by the left and right nozzles or nozzle patterns may be non-parallel. For example, as shown in FIG. 18, a nozzle gas flow path 1801 and exit axis can be angled inward, for example at an angle of approximately 0.5-20 degrees inward, and preferably approximately 2-6 degrees inward. This angle may align the ventilation gas flow entering the nostril airway with the nostril airway, which may optimize flow characteristics, and facilitate creating laminar positive pressure flow with minimal disturbance and resistance.

FIGS. 14 and 15 describe the gas flow path pattern entering the nose. As an example, a dual left and dual right gas delivery nozzle pattern is used in this description. As can be seen, the combined gas flow pattern created in the nostril airway by the dual nozzle arrangement may distribute the delivered flow and velocity profile evenly across the proper cross-section of the nostril airway path. This may improve positive pressure formation before the gas travels deep into the nasal airway, improve laminar flow, and reduce turbulence that could be irritating to the user. For example, if the flow profile is more concentrated, a high velocity flow can impinge on a nerve receptor on the inside of the nasal passage, which could be intolerable to the user. In testing, more focused flow profiles were found to irritate users, whereas a more distributed flow profile was found to be tolerable. The spacing, angle, rotational position, and or orientation of the nozzles can be adjustable, or the mask can be available in different sizes so that the flow pattern created by the nozzles matches the size and shape of the user's nasal anatomy. For example, when dual nozzles are used, the nozzle positions can be rotated to rotate the rotational position of the oval pattern created by the pair of nozzles, so that the oval pattern matches with the oval orientation of the user's nostril airway.

Figure 19:
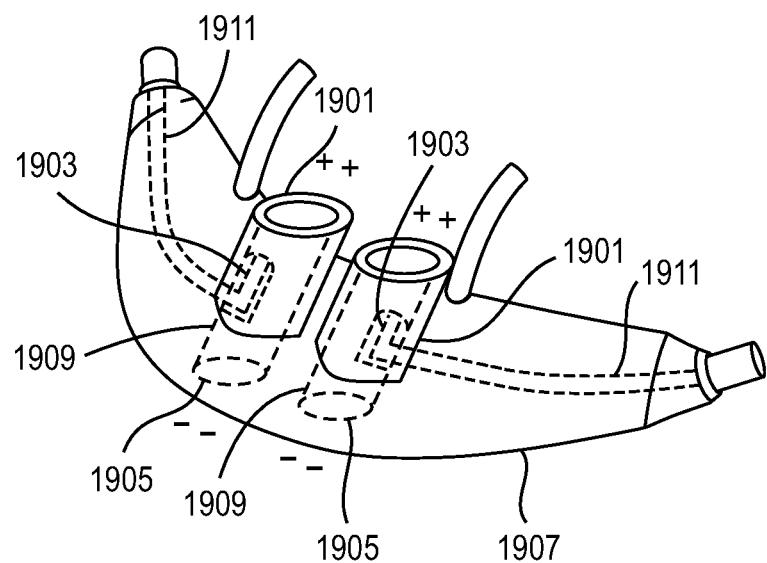
FIG. 19 shows an embodiment of the mask shown in FIG. 5 with a jet pump throat with a Venturi inlet at the bottom of the mask manifold.
Figure 20:
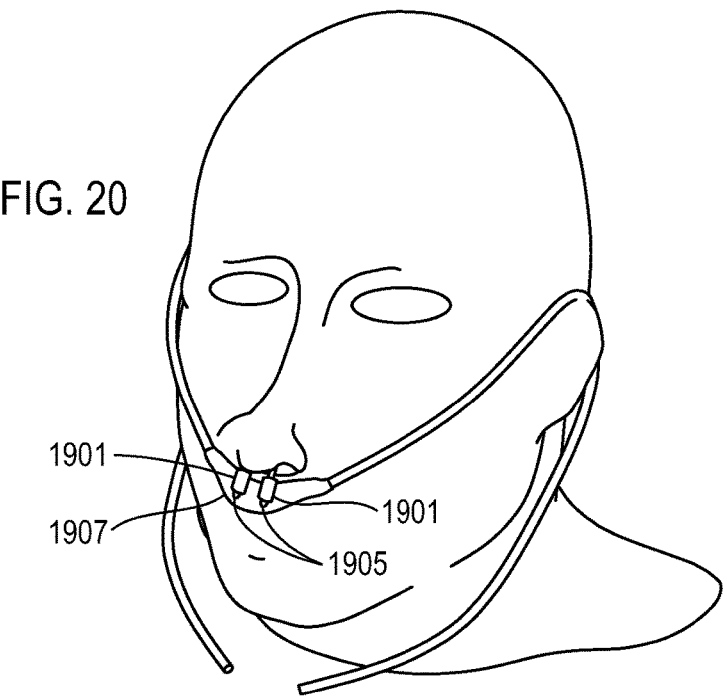
FIG. 20 shows a mask worn by a user with a jet pump throat with a Venturi inlet at the top of the manifold near the base of the throat.

Nasal Mask with Jet Pump Throat:

In addition, as shown in FIGS. 19 and 20, the mask can include a jet pump throat section 1901. FIG. 19 has an entrainment port 1905 opening on bottom of a manifold 1907. FIG. 20 shows same throat section 1901, but has the entrainment ports 1905 on top of the manifold at the base of the throat section 1901. In FIG. 19, ambient air may be entrained through the bottom of the manifold 1907. In FIG. 20, ambient air may be entrained past the top of the manifold 1907.

The jet pump throat section 1901 can be useful in creating consistent performance of the ventilation system from one person to another, by minimizing the effect of patient anatomy on performance. The jet pump throat section 1901 can also be useful in dampening the sound that is generated by the high velocity gas exiting gas delivery nozzles 1903 and entraining ambient air. The jet pump throat section 1901 can alternatively include entrainment ports 1905 at the base of the jet pump throat section 1901 as shown in FIG. 20, or a manifold 1907 can include a through-hole 1909 that functions as an entrainment aperture as shown in FIG. 19, which extends through the thickness of the manifold 1907 from the bottom of the manifold 1907 to the top of the manifold 1907 and which is in communication with the gas delivery nozzle 1903. The throat section 1901 of the mask shown in FIG. 19 can also be used to reduce the sound generated by the Venturi and as such this embodiment may be useful in a sleep apnea application, in which minimal sound is a critical performance requirement. The entrainment port 1905 is shown at bottom of manifold 1907 in FIG. 19, but can be on the side of the jet pump throat section 1901, for example, near the nozzle 1903. Gas delivery lumens 1911 may be included from either proximal end of the manifold 1907.

The nozzle in FIG. 19 can be any type of nozzle. In FIG. 19, there may be a throat option that is part of the manifold and outside of the nose.

Figure 21:
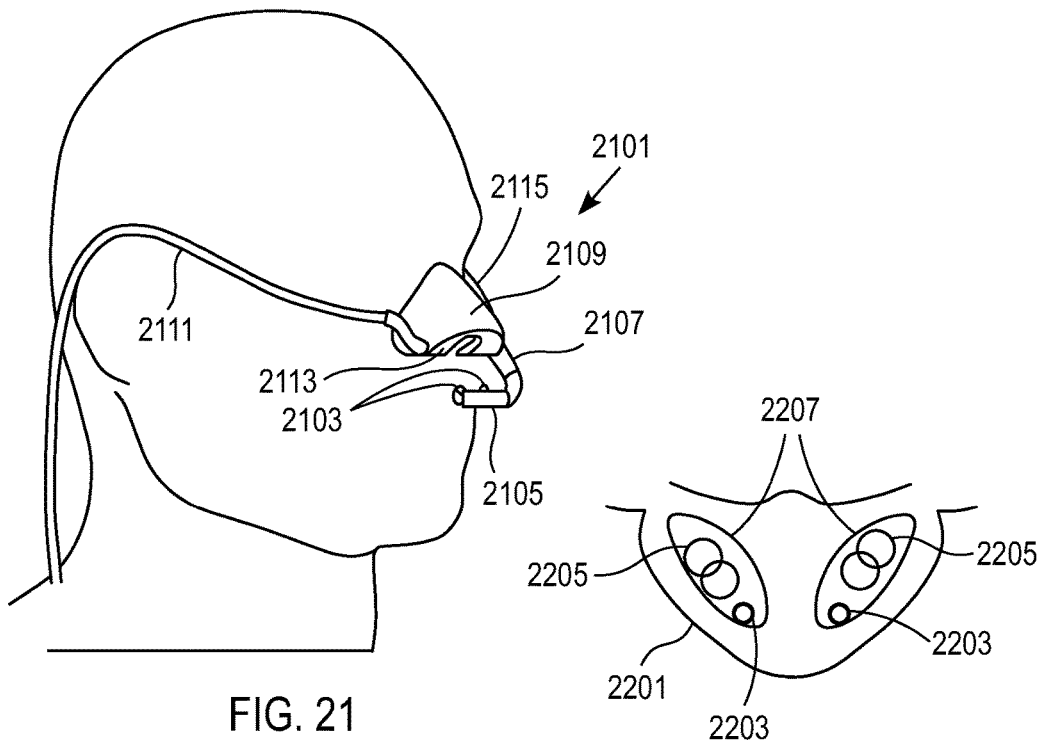
FIG. 21 shows an alternative embodiment of the nasal mask where the gas delivery nozzles are positioned under the nose by a nose piece with extension arm.

Other Mask Form Factors:

FIG. 21 describes an alternative embodiment of a nasal mask 2101 in which gas delivery nozzles 2103 are positioned in the correct location under the nose by use of a horizontal extension arm 2105 attached to a vertical extension arm 2107 that extends down from a nose piece 2109 that is configured to be placed on and secured to the front of the nose. The nose piece 2109 can be secured to the nose by a variety of means, such as by using gas delivery tube 2115 and pressure sensing tube 2111 connected to the nasal mask 2101 to secure the nose piece 2109 to the face. The nose piece 2109 can also be secured to the nose by other means, such as by straps, adhesives, a friction fit, or combinations thereof.

The vertical extension arm 2107 can be adjustable to position the gas delivery nozzles 2103 at the appropriate distance from the user, and the horizontal extension arm 2105 can be rotate-ably adjustable to angle the gas delivery nozzles 2103 correctly to be in alignment with the nostril airway. The spacing between the gas delivery nozzles 2103 can be adjustable, for example by a linear adjustment in the horizontal arm.

Breathing pressure sensing ports (not shown) may extend upward from the nose piece 2109 to be positively located at, near or inside the entrance to the nose. The nose piece 2109 may include a shelf 2113 at its bottom end which is used to position against the outside of the nostril rim. The breathing pressure sensing tube 2111 may be attached to one side of the nose piece 2109, the user's right side in FIG. 21, and the gas delivery tube 2115 may be attached to the opposite side.

The nasal mask 2101 may also include additional sensing functions such as a CO2 gas sampling port (not shown) and conduit extending to a capnometer (not shown), which can be included by integrating a secondary channel into the gas delivery tubing or pressure sensing tubing, and integrating the requsite channel into the mask nose piece and or extension arms. The nose piece 2109 may also prevent gas being delivered from the gas delivery nozzles 2103 from being directed toward the eyes when the nasal mask 2101 is not fitted properly to the user.

The nasal mask 2101 may also include additional sensing functions such as a $CO_2$ gas sampling port (not shown) and conduit extending to a capnometer (not shown). The nose piece 2109 may also prevent gas being delivered from the gas delivery nozzles 2103 from being directed toward the eyes when the nasal mask 2101 is not fitted properly to the user.

This embodiment of the invention may use the angle of the medial aspect of the bridge of the nose to align the therapy to the patient. During testing, it was determined that the optimal performance was achieved when the gas delivery nozzles 2103 were aimed parallel to the bridge of the nose to align the jets of ventilation gas with the nares. The gas delivery nozzles 2103 of the nasal mask 2101 may be aimed parallel to the nose piece 2109, such that by placing the nose piece 2109 on the bridge of the nose, the gas delivery nozzles 2103 may be parallel to the bridge of the nose.

Figure 22:
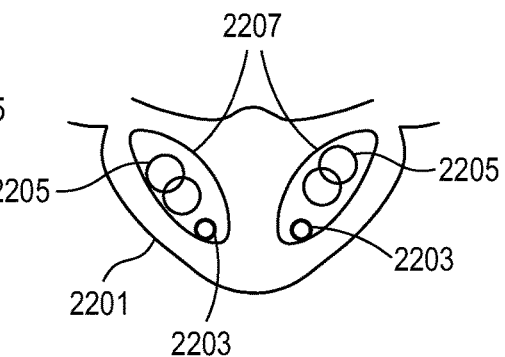
FIG. 22 shows the pressure sensing and gas delivery flow patterns of the nasal mask of FIG. 21 in the nostril airway.

If there is some misalignment, performance may degrade. The gas delivery nozzles 2103 preferably are kept within 10 degrees of being properly aligned with a nasal opening and an axis of the nares. As such, when a patient moves their nose to the left or right (e.g. by moving your jaw in an exaggerated manner), the nasal mask 2101 may follow the nose, ensuring that the gas delivery nozzles 2103 remain aligned with the centerline of the nose, and therefore the nostrils. In FIG. 22, gas delivery patterns 2205 may include two intersecting circles to create an effective oval pattern, which are for example generated by dual nozzles, as explained previously for the purpose of developing a laminar cross section of flow and positive pressure in the nostril airway.

FIG. 22 shows a bottom view of a nose 2201 and how the nasal mask 2101 of FIG. 21 is aligned with the nose 2201. A breathing pressure sensing location 2203 and gas delivery patterns 2205 are superimposed on the bottom view image of a nose 2201 and the nostril airway 2207 as depicted by the two large oval shapes. Gas delivery pattern 2205 and nasal air pressure sensing locations 2203 are indicated by the large and small circles, respectively. The patterns 2205 are generated in this example by two gas delivery nozzles for the left and right nostril, which applies to other mask embodiments of the invention in addition to the mask of FIG. 22.

The nasal air pressure sensing ports may be protrusions to help achieve a positive location of the sensing ports in the breath path in the nares. The gas delivery ports may be positioned such that the gas delivery path has a clear path to the nostril airway. There may be two or more sizes of nasal mask 2201, and or adjustment features in the mask, so that the sensing ports and gas delivery zones are properly aligned with the nasal airway path. The previous figures describe that the sensing locations must be in proximity to the entrance of the nostril, either inside, coplanar to the entrance, or slightly outside but if outside no more than 5 mm away from the entrance, whereas the gas delivery nozzle tips are located a distance from the entrance to the nostrils, for example 10-25 mm away. This configuration may allow the nasal mask 2201 to take advantage of the jet pump geometry, while not sacrificing sensing accuracy, so that the ventilator is in proper synchrony with the patient. Also, the gas flow profile may become more organized before entering the patient's nostril, rather than a turbulent jet entering the nostril, which would be quite uncomfortable and intolerant to the patient.

Figure 23:
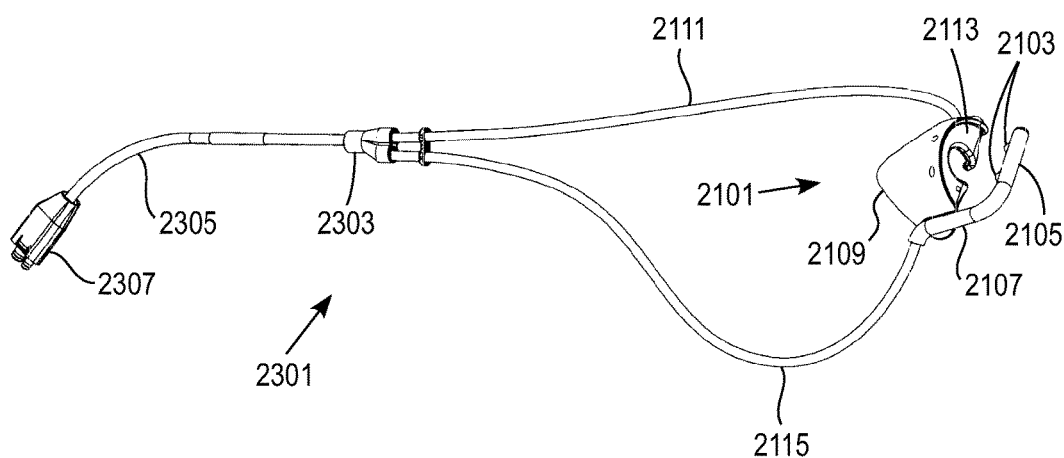
FIG. 23 shows the mask assembly of the nasal mask shown in FIG. 21.

FIG. 23 shows an isometric view of the patient circuit assembly 2301 of the nasal mask 2201 shown in FIG. 21. A Y connector 2303 joining a breathing pressure sensing tube 2111 and gas delivery tube 2115 is shown, and combined tubing 2305 and a ventilator connector 2307 at a proximal end of the patient circuit are shown.

Figure 24:
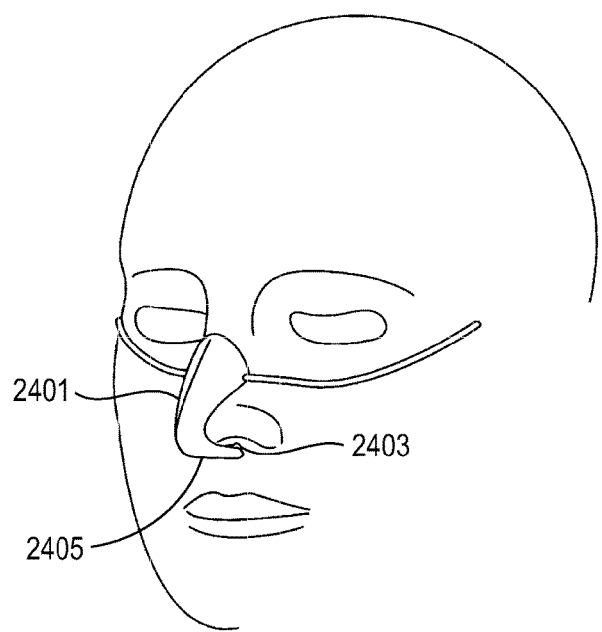
FIG. 24 shows an alternate embodiment of the nasal mask shown in FIG. 21 in which the gas delivery nozzles are positioned under the nose with an extended nose piece.
Figure 25:
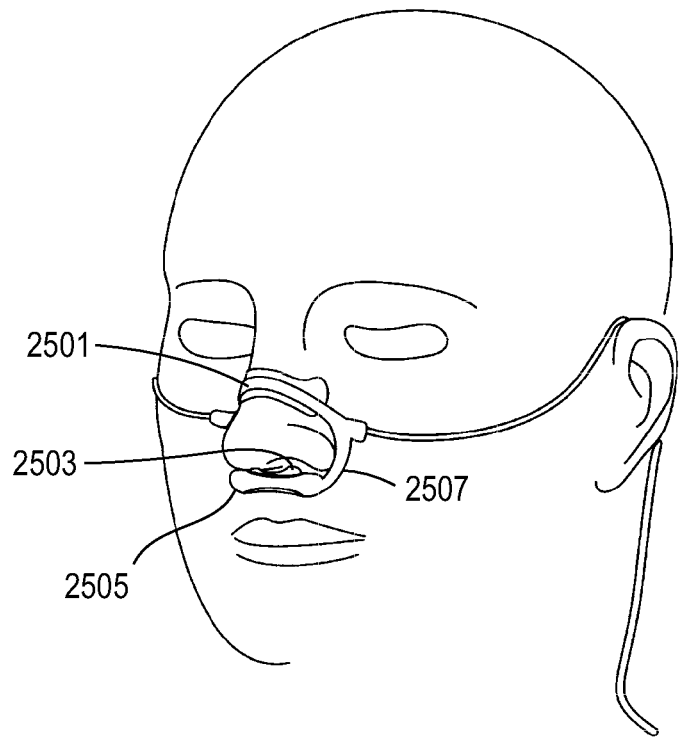
FIG. 25 shows an embodiment of the nasal mask shown in FIG. 21 with a minimized nose piece and streamlined vertical and horizontal arms.

FIGS. 24 and 25 describe aesthetically streamlined versions of the nasal mask shown in FIG. 21. Features of the nose pieces 2401, 2501 may be trimmed to optimize the comfort and to minimize the obtrusiveness to the user. In FIG. 24, the gas delivery nozzles 2403 may be positioned under the nose by an extension 2405 of the nose piece 2401 itself versus the vertical extension arm of the mask in FIG. 21. In FIG. 25, the nose piece 2501 may be a strip on the top of the bridge of the nose and the gas delivery nozzles 2503 may be positioned by use of a streamlined vertical arm 2505 and a streamlined horizontal arm 2507.

Figure 26:
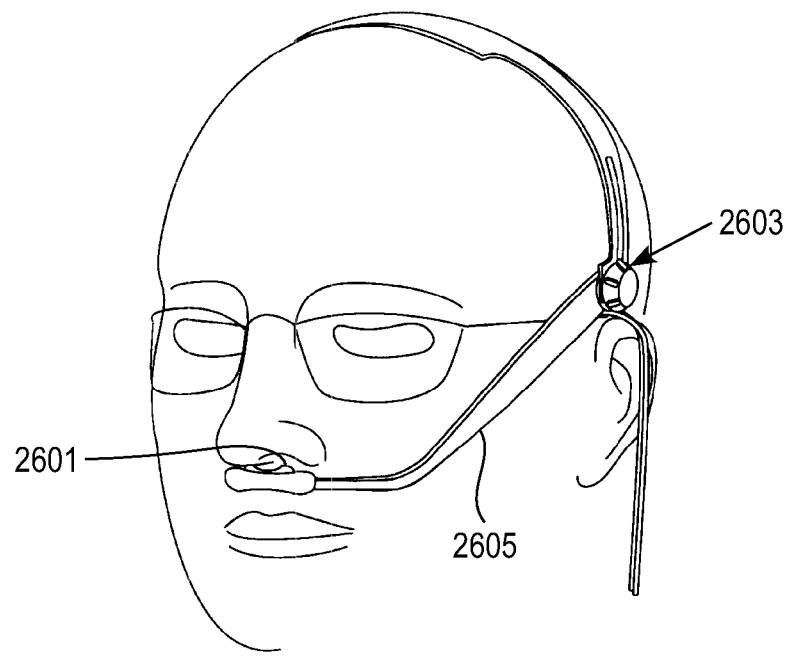
FIG. 26 shows an embodiment of the nasal mask shown in FIG. 21 in which the gas delivery nozzles are positioned under the nose by a head gear and bracket.

FIG. 26 shows a version of the mask shown in FIG. 21 in which gas delivery nozzles 2601 are positioned under the nose at the correct location using head gear 2603 with an extension arm 2605. The head gear 2603 and extension arm 2605 can be adjustable to position the gas delivery nozzles 2601 and breathing pressure sensing ports (not shown) in the correct location.

The following tables list exemplary values only and are not to be construed as limiting the disclosure.

TABLE 1

Nasal Mask Exemplary Key Dimensions and Values

| Feature | Preferred/ideal | Range |
| --- | --- | --- |
| Nozzle diameter: | 0.033 in | .010-.050 in |
| Flow rate delivered to nozzle: | 30 lpm | 6-40 lpm |
| Input pressure delivered to nozzle: | 35 psi | 5-60 psi |
| Throat length, if included: | .6-1.0 in | .3-1.5 in |
| Throat typical cross sectional area, if included: | 0.04 in$^2$ | 0.02-0.06 in$^2$ |
| Nozzle distance to proximal edge of nose: | 0.5-1.2 in | 0.3-1.3 in |

TABLE 2

Exemplary Ventilatory Support Parameters

| Parameter | Range | Preferred (Adult*) |
|---|---|---|
| Lung Volume Augmentation (%) | 10-150% | 15-65% |
| WOB reduction (%) | 5-80% | 10-50% |
| Lung Pressure increase (cmH$_2$O) | 1-30 | 3-20 |
| Upper Airway pressure increase (cmH$_2$O) | 3-34 | 7-25 |
| Lung Pressure or Volume Waveform | (1) | R |
| Entrained ambient air (% of Ventilator gas delivery) | 10-300% | 50-100% |
| Gas exit speed out of gas delivery nozzle (m/sec) | 25-350 | 50-200 |
| Ventilator Output flow rate, average (lpm) | 5-40 | 10-20 |
| Gas Delivery Tubing outer diameter (mm) | 3-7 | 4-6 |
| Ventilator Output Pressure (psi) | 10-60 | 20-40 |
| Ventilator Drive Pressure (psi) | 10-80 | 20-50 |
| Ventilator Operating Pressure (psi) | 5-40 | 25-35 |
| Ventilator Output Volume (ml) | 10-750 | 50-350 |
| Ventilator Output Pulse Time (sec.) | 0.100-1.25 | 0.200-0.750 |
| Therapy's nominal source gas consumption (lpm) | 0.5-6.0 | 2-4 |
| Ventilator Output Synchronization (ms) | variable depending on comfort and need (25-500 ms delay) | variable depending on comfort and need (75-250 ms delay) |
| Ventilator Output Waveform | (1) | Descending |

TABLE 3

Additional Exemplary Dimensions, Values and Materials

| Feature | Range | Preferred Range |
|---|---|---|
| Dimensions | | |
| Gas delivery hose, ID (mm) | 2.0-7.0 | 2.5-4.5 |
| Gas delivery hose, Length (ft), ambulating with wearable system | 2-6 | 2.5-4 |
| Gas delivery hose, Length (ft), ambulating with stationary system | 20-75 | 40-60 |
| Gas delivery hose, Length (ft), sleeping | 4-15 | 6-10 |
| Jet Nozzle, Length (mm) | 0.5-15 | 2-10 |
| Manifold Length (mm) | 20-160 mm | 30-80 mm |
| Manifold spontaneous breathing gas flow path volume | 0 ml | 0 ml |
| Manifold pressure sensing line diameter (in) | .008-.055 | .015-.040 |
| Manifold breathing resistance (cmH$_2$O @ 60 lpm) | 0 | 0.01-0.10 |
| Breathing sensing port, distance to nose (mm) | −5 to 2 | −10 to 5 |

| Materials | Types | Preferred |
|---|---|---|
| Gas delivery hose | PP, PE, PS, PVC | PE |
| Cannula | PU, PVC, Silicone | PVC, Silicone |
| Manifold | PVC, Silicone, PU, PE, Polysolfone | PVC, Silicone |
| Jet Nozzle | Metal, Ultem, Nylon, LCP, PVC, PC, ABS, PEEK | PVC |

(1) Square, Rounded, Descending, Ascending, Sinusoidal, Oscillating.
* Dimensions listed are exemplary and for average sized adults; pediatric sizes 20% less, neonatal sizes 50% less.
Diameters listed are effective diameters (average cross sectional dimension).

Figure 27:
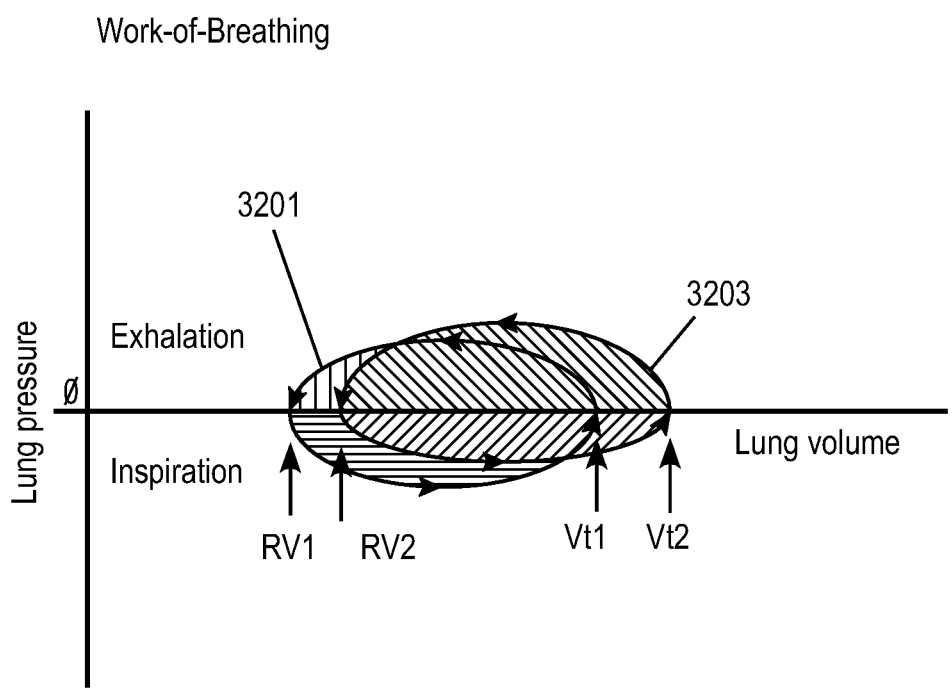
FIG. 27 graphically shows how the patient's work of breathing may be beneficially affected by the invention when the invention is used for lung disease or neuromuscular disease applications.

FIG. 27 describes the mechanism of action of the invention, and how the patient's work of breathing may be beneficially affected by the invention, when the invention is used for lung disease or neuromuscular disease applications. The patient's lung volume may be graphed as a function of lung pressure, the area inside the curve representing work, typically expressed in Joules per Liter (J/L), and for a normal healthy adult can be 0.3-0.6 J/L. For a respiratory compromised patient, 4-10 times more work can be required to breathe during rest, and even more during exertion, to overcome the diseased state of the tissue, for example to overcome static and dynamic hyperinflation as in the case of COPD, or to overcome high airways resistance as in the case of fibrosis or ARDS.

In the graph shown, the area inside the curve below the pressure axis is the inspiratory WOB, and the area defined by the area inside the curve above the pressure axis is the expiratory WOB. The arrows show the progression of a single breath over time, starting from RV to VT then returning from VT to RV. RV1 and VT1 are the residual volume and tidal volume without the therapy. Line 3201 represents spontaneous breathing without non-invasive open nasal ventilation. Line 3203 represents spontaneous breathing with non-invasive open nasal ventilation, with inspiratory augmentation and positive end-expiratory pressure (PEEP) therapy. RV2 and VT2 are the residual volume and tidal volume with the therapy. As can be seen, RV increases with the therapy because in this example, expiratory flow is provided as part of the therapy, which may increase residual volume. Importantly, VT is increased with the therapy and is increased more that the RV is increased, indicating that more volume is entering and leaving the lung as a result of the therapy. The increase in tidal volume is considered clinically efficacious, however is technically challenging to achieve in an open ventilation, non-invasive and minimally obtrusive system. As is shown in the graph, the patient's inspiratory WOB with the invention ON may be about 25% less than the patient's inspiratory WOB with the invention OFF. Also, inspiratory lung pressure increases (is less negative) and tidal volume increases, and optionally exhaled pressure increases if the therapy is provided during exhalation. While residual volume increases in the example shown because the ventilator is providing gas in this example during the expiratory phase, the ventilation parameters can be titrated to not effect residual volume, and because of the ability of the patient to exercise their lung muscles when receiving the therapy, the patient's lung mechanics may remodel in the case of COPD, actually causing a reduction of residual volume to a more normal value. In the graph shown, the waveform with therapy assumes an early inspiratory trigger time for the ventilator inspiratory phase therapy output, and that the volume output is delivered within the patient's inspiratory time. Optionally, however, different delivery waveforms and delivery synchronizations can be performed, which may adjust the WOB curve. For example, the ventilator inspiratory phase therapy can be delivered late in the person's inspiratory cycle, with delivery completing at the end of inspiration, and delivered with a square or ascending waveform profile. In this case the WOB curve with therapy will be tilted upward to the right of the curve, such that inspiration ends and transitions to exhalation at a point above the lung pressure zero axis.

Figure 28:
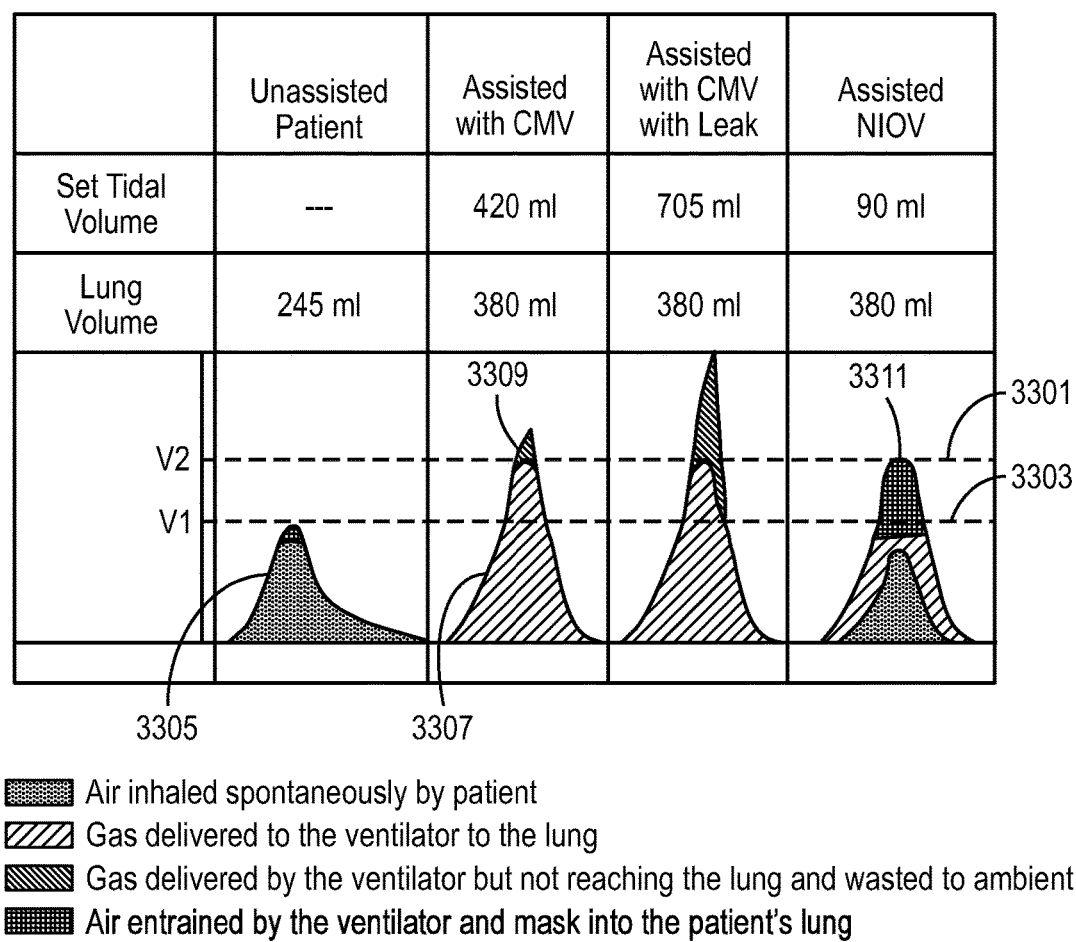
FIG. 28 graphically shows lung volume on the x-axis and lung pressure on the y-axis to illustrate how the lung volumes achieved with NIOV on a lung simulator bench model in comparison to conventional ventilation.

FIG. 28 graphically illustrates the lung volumes achieved with NIOV on a lung simulator bench model in comparison to conventional ventilation. In all the waveforms the simulated patient is spontaneously breathing at the same inspiratory effort which results in a tidal volume of 245 ml, and the clinical goal is to increase the patient's tidal volume from 245 ml 3301 to 380 ml 3303. In the first waveform from left to right in the graph, the patient's breath 3305 is un-assisted and thus the patient receives a tidal volume of 245 ml. In the next waveform, the simulated patient with the same effort is assisted with a traditional closed system ventilator, such as with a sealed breathing mask or cuffed airway tube. The ventilator output 3309 is set to a level to achieve the desired "assisted" tidal volume of 380 ml. The ventilator is set to 420 ml to achieve this goal, as there is a discrepancy between the gas delivered to the lung by the ventilator versus the gas delivered by the ventilator but not reaching the lung and wasting to ambient 3307. In the third waveform, a small leak is introduced in the conventional ventilator system, such as would be done in the case of weaning the patient off of the ventilator. To achieve the desired "assisted" tidal volume of 380 ml, the ventilator must now be set at 705 ml. In the second and third waveforms, it can also be seen that all of the volume received by the patient's lung originates from the ventilator, which it must in these conventional systems. In the forth waveform, the patient is assisted with the NIOV, and as can be seen, the NIOV ventilator output only has to be set at 90 ml to achieve desired "assisted" level of 380 ml. In this case, only some of the 380 ml tidal volume comes from the ventilator, and a substantial portion of the 380 ml comes from entrainment and spontaneously inspired ambient air 3311, therefore making the NIOV system far more efficient, comfortable, and healthier, than the other systems.

Figure 29:
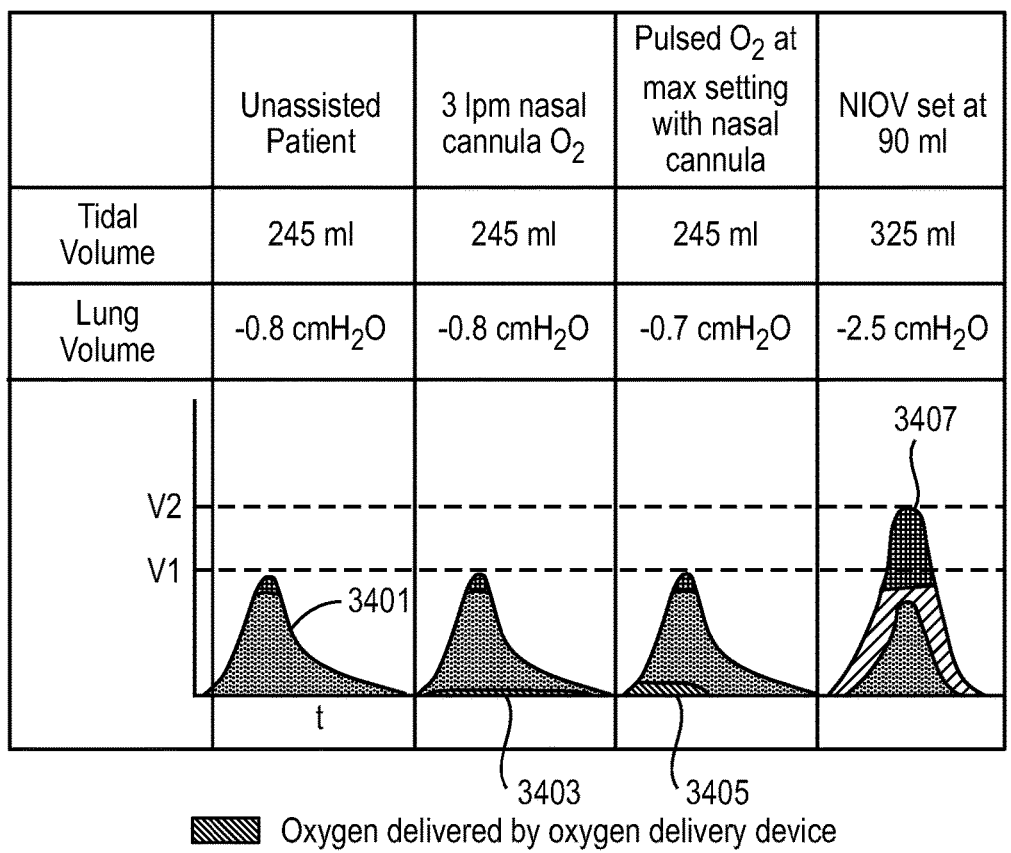
FIG. 29 graphically shows the lung volumes achieved with NIOV in comparison to oxygen therapy, using the lung simulator bench model.

FIG. 29 graphically shows NIOV in comparison to oxygen therapy, using the lung simulator bench model. In the first waveform on the left, the patient is unassisted and breathes at an effort of −0.8 cmH2O, generating 248 ml of inspired tidal volume 3401. In the second waveform and third waveform, the patient receives continuous flow 3403 and pulsed flow 3405 of oxygen respectively via nasal cannula, with no or negligible effect on lung pressure and tidal volume. In the forth waveform, NIOV 3407 is used which shows a marked increase in lung pressure and tidal volume, thus indicating that NIOV helps in the work-of-breathing as described earlier, despite the fact that NIOV is an open airway system.

FIGS. 30A-30L show exemplary ventilation gas delivery profiles of the invention and their respective effect on lung volume and lung pressure.

FIGS. 30A, 30D, 30G and 30J show exemplary pressure and/or flow waveforms delivered by the ventilator. FIG. 30A describes a square waveform 3501 delivered during the complete inspiratory cycle; FIG. 30D describes an ascending and descending waveform 3503; FIG. 30G describes a square waveform 3507 delivered for the first part of the patient's spontaneous inspiratory time; FIG. 30J shows a multilevel amplitude waveform 3509 with a first amplitude 3511 delivered during the inspiratory phase and a second amplitude 3513 during the expiratory phase, where the second amplitude 3513 for example is used to deliver positive end-expiratory pressure (PEEP), which in some clinical applications will be efficacious. Other waveforms are also included in the invention, such as a descending trapezoidal or ascending trapezoidal square wave. The pressure and flow rate output from the ventilator into the gas delivery tubing is typically in the 5-40 psi and 6-30 lpm range.

FIGS. 30B, 30E, 30H and 30K describe the lung volume being delivered by the therapy including a ventilator output 3515 and an entrained volume 3517.

FIGS. 30C, 30F, 30I and 30L show the lung pressure without therapy represented by the dashed line 3519, and the resultant lung pressures with the therapy represented by the solid line 3521, showing a positive inspiratory pressure in FIG. 30C for the entire inspiratory phase, a positive inspiratory pressure for part of the inspiratory phase in FIGS. 30F and 30I, with therapy extending into exhalation 3523, and an elevated negative inspiratory pressure in FIG. 30L.

FIGS. 36A-36L describe additional exemplary ventilation gas delivery profiles of the invention and their respective effect on lung volume and lung pressure.

Figure 31A:
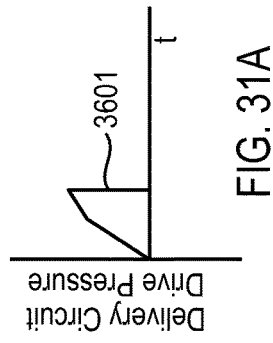
FIG. 31A graphically shows an ascending waveform gas delivery pressure, according to one embodiment.
Figure 31B:
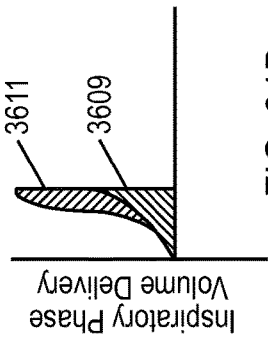
FIG. 31B graphically shows the volume delivery of FIG. 31A.
Figure 31C:
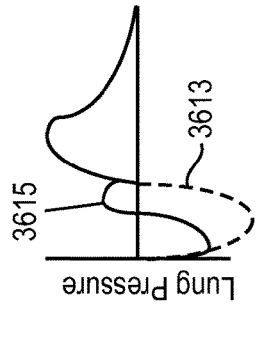
FIG. 31C graphically shows resulting lung pressure of FIG. 31A.
Figure 31D:
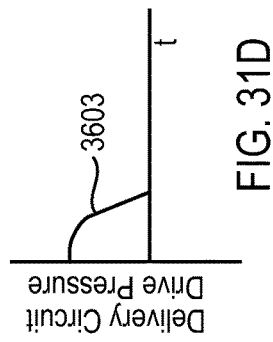
FIG. 31D graphically shows a descending waveform gas delivery pressure, according to one embodiment.
Figure 31E:
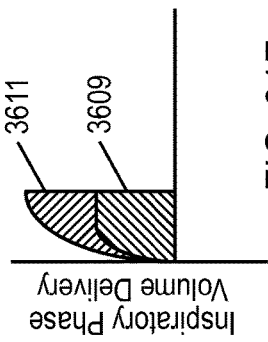
FIG. 31E graphically shows the volume delivery of FIG. 31D.
Figure 31F:
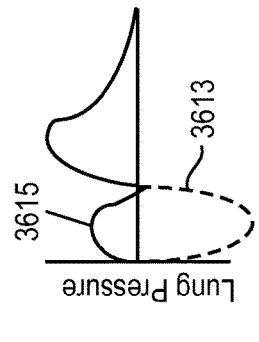
FIG. 31F graphically shows resulting lung pressure of FIG. 31D.
Figure 31G:
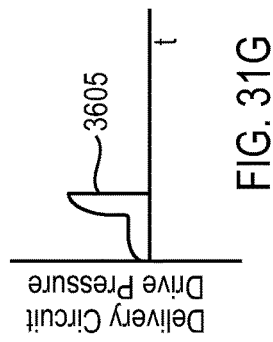
FIG. 31G graphically shows a two-stage amplitude waveform gas delivery pressure for a portion of the inspiratory phase, according to one embodiment.
Figure 31H:
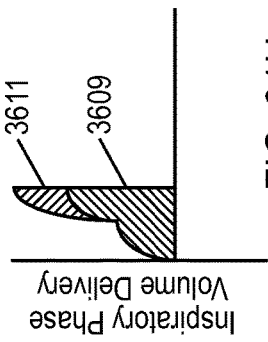
FIG. 31H graphically shows the volume delivery of FIG. 31G.
Figure 31I:
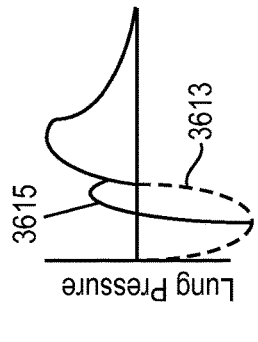
FIG. 31I graphically shows resulting lung pressure of FIG. 31G.
Figure 31J:
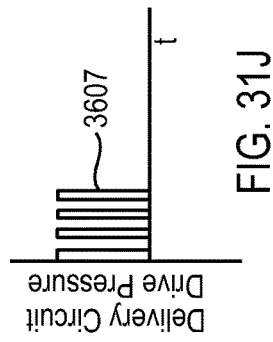
FIG. 31J graphically shows an oscillatory waveform gas delivery pressure, according to one embodiment.
Figure 31K:
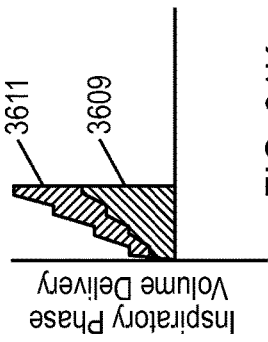
FIG. 31K graphically shows the volume delivery of FIG. 31J.
Figure 31L:
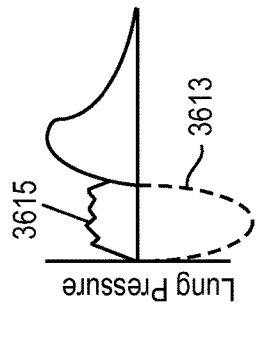
FIG. 31L graphically shows resulting lung pressure of FIG. 31J.

FIG. 31A describes an ascending waveform 3601. FIG. 31D describes a descending waveform 3603. FIG. 31G describes a multi-level waveform 3605 with a lower amplitude in the first portion of the inspiratory phase, for example to deliver the necessary oxygen molecules to the lung early in the breath phase, and a higher amplitude in the second portion of the inspiratory phase, for example to deliver the mechanical support portion of the therapy to help the work of breathing. FIG. 31J describes an oscillatory waveform 3607, which may be use the gas supply more efficiently while producing nearly the same Venturi, entrainment and therapeutic effect.

FIGS. 31B, 31E, 31H and 31K describe the lung volume being delivered by the therapy including a ventilator output 3609 and an entrained volume 3611.

FIGS. 31C, 31F, 31I and 31L show the lung pressure without therapy represented by the dashed line 3613, and the resultant lung pressures with the therapy represented by the solid line 3615.

The lung pressure resulting from the therapy may be governed by a combination of factors: the gas delivery circuit pressure, the jet pump design and configuration, the patient's lung compliance and airway resistance, the patient's breathing effort, the timing of the ventilator output relative to the patient's inspiratory phase, and the ventilator output waveform. Typically, however, a gas delivery circuit pressure of 30 psi delivering 100 ml with a square waveform, and delivered for 500 msec starting at the beginning of the patient's inspiratory phase, may increase lung pressure by 5-15 cmH2O. And, typically a gas delivery circuit pressure of 30 psi delivering 250 ml with a trapezoidal waveform, and delivered for 700 msec during the majority of the patient's inspiratory phase, may increase lung pressure by 10-25 cmH2O. The gas delivered by the ventilator can be oxygen, air, oxygen-air mixtures, or therapeutic gases such as helium. In a main mechanism of action of the invention, the patient's lung pressure and lung volume is increased, which allows the patient to exert them self without being limited by fatigue and dyspnea. In another main mechanism of action of the invention, the patient reduces their breathing effort in response to the pressure and volume support provided by the therapy, thus resulting in no change in total lung volume from the therapy, but resulting in a reduced work of breathing. In another main embodiment of the invention, a combination of the above two mechanisms of action can occur.

Figure 32:
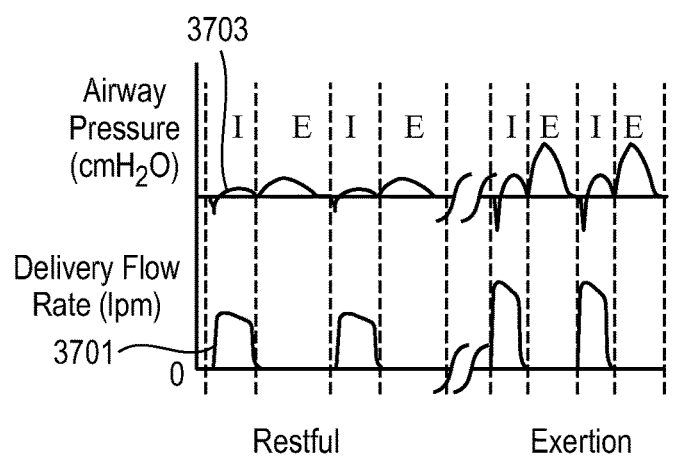
FIG. 32 graphically shows the timing and amplitude of a breath frequency modulated gas flow amplitude delivery, according to one embodiment.

FIG. 32 is a diagram of timing and gas flow delivery, according to one embodiment. Amplitude of gas flow delivery rate 3701 modulates with respiratory rate to affect airway pressure 3703. The faster the respiratory rate, the higher the amplitude. The volume delivery may be maintained at a constant rate, unless changed by the user, between the restful state and exertion state. However, the amount of power delivered by the system may be higher during the exertion state, because the faster flow rate entrains more gas, which produces more power and higher lung pressures during inspiratory phase. Further, the delivery time of the delivered flow can be adjusted by the user as a percentage of the breath period. For example, if the breath period is 3 seconds, a 25% delivery time setting would equal a delivered flow pulse width of 0.75 seconds. The delivered flow pulse width would change with the breath rate; however, it may continue to be 25% of the breath period (unless changed by the user). The setting can be set for example in the range of 15% to 70% of the breath period. The setting may be independent of the volume setting. For example, a setting of 25% versus 40% may still deliver the same set volume, and may merely deliver the set volume at different flow rates. The algorithm for adjusting the delivered flow pulse time may, for example, look at the preceding 3 to 5 breaths to determine what the current breath period is, and may have a correction factor to rule out outlier breaths.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A system for supplying ventilatory support, comprising:
    a gas delivery source;
    a gas delivery circuit;
    a non-sealing nasal interface configured to be placed under a nose of a patient and to communicate with the patient's nostril airway while allowing the patient to breathe ambient air;
    a nozzle associated with the non-sealing nasal interface and configured to be positioned a distance from a nostril entrance of the patient's nostril airway when the non-sealing nasal interface is placed under the nose of the patient, the nozzle being connectable to the gas delivery circuit and the gas delivery source;
    wherein the nozzle is configured to deliver a gas flow cone defined by the gas exiting the nozzle, such that when the non-sealing nasal interface is placed under the nose of the patient, the gas flow cone intersects with an internal wall of the patient's nostril airway at an intersecting point, the area inside the gas flow cone and the area within the patient's nostril airway distal to the intersecting point defining a positive pressure area wherein a laminar positive pressure flow is developed, the area outside the gas flow cone defining a negative pressure area entraining ambient air into the patient's nostril airway; and
    wherein a combination of gas from the gas delivery source and air entrained into the patient's nostril airway provide ventilatory support.

2. The system of claim 1, wherein the non-sealing nasal interface comprises a manifold, and wherein the manifold comprises the nozzle.

3. The system of claim 2, wherein the manifold is configured to position the nozzle at the distance away from the nostril entrance, and configured to position the nozzle at an angle relative a centerline of the nostril airway.

4. The system of claim 1, further comprising one or more sensors.

5. The system of claim 4, wherein the one or more sensors comprise a sensing channel that extends away from the nozzle toward the nose terminating in the positive pressure area.

6. The system of claim 4, wherein the one or more sensors comprise a sensing channel that extends distally away from the nozzle.

7. The system of claim 6, wherein the sensing channel extends into the nose of the patient.

8. The system of claim 6, wherein the sensing channel extends to within approximately +/−5 mm from the nostril entrance.

9. The system of claim 1, further comprising two or more nozzles per nostril.

10. The system of claim 1, wherein the nozzle is an oval-shaped gas delivery nozzle orifice.

11. The system of claim 1, wherein the nozzle comprises an array of multiple gas delivery nozzles arranged in a circular or oval pattern.

12. The system of claim 1, further comprising a jet pump throat comprising a flow path.

13. The system of claim 12, wherein the jet pump throat is associated with a manifold, and the nozzle is associated with a jet pump throat flow path through the jet pump throat.

14. The system of claim 13, wherein the manifold comprises an entrainment port in communication with the jet pump throat flow path.

15. The system of claim 1, wherein the nozzle angles inward.

16. The system of claim 15, wherein the nozzle angles inward at an angle of 1 degree to 20 degrees.

17. The system of claim 1, wherein the nozzle creates an oval shaped gas flow cone within a nostril airway.

18. The system of claim 17, wherein the nozzle is rotatably adjustable.

19. The system of claim 1, wherein the nozzle comprises at least one left nozzle and at least one right nozzle, wherein the spacing between the at least one left nozzle and the at least one right nozzle is adjustable.

20. The system of claim 19, wherein the at least one left nozzle and the at least one right nozzle are rotatably adjustable.

21. The system of claim 1, wherein spacing between the nostril entrance and nozzle is adjustable.

22. The system of claim 1, wherein the non-sealing nasal interface is available in different sizes, differing in nozzle spacing, nozzle rotational orientation and nozzle distance to nostril entrance.

23. The system of claim 1, wherein a negative pressure of the negative pressure area is less than ambient.

24. The system of claim 23, wherein the negative pressure of the negative pressure area is −5 cmH$_2$O to −28 cmH$_2$O.

25. The system of claim 1, wherein the positive pressure of the positive pressure area is greater than ambient.

26. The system of claim 25, wherein the positive pressure of the positive pressure area is approximately 0.01 psi to approximately 0.50 psi.

27. The system of claim 1, wherein the nozzle is positioned at a distance of up to 1.5 inches from the nostril entrance of the patient's nostril airway when the non-sealing nasal interface is placed under the nose of the patient.

28. The system of claim 1, wherein delivery of gas through the nozzle is synchronized with a breathing pattern of the patient.

29. The system of claim 1, wherein the gas from the gas delivery source is controlled by a wearable ventilator.

30. The system of claim 1, wherein ventilatory support comprises reducing the work of breathing to treat respiratory insufficiency.

31. The system of claim 1, wherein ventilatory support comprises elevating airway pressure to treat sleep apnea.

32. The system of claim 1, wherein the non-sealing nasal interface comprises a connector for coupling the system to a bridge of the nose and aligning the nozzle with the nostril entrance of the patient's nostril airway.

33. The system of claim 32, wherein the aligning of the nozzle with the nostril entrance of the patient's nostril airway comprises adjusting the angle of the nozzle to be in alignment with the centerline of the nostril airway.

34. A method for providing portable non-invasive open-airway ventilatory support, the method comprising:
providing a non-sealing nasal interface configured to be placed under a nose of a patient and to communicate with the patient's nostril airway while allowing the patient to breathe ambient air; and
providing a nozzle associated with the non-sealing nasal interface and configured to be positioned a distance from a nostril entrance of the patient's nostril airway when the non-sealing nasal interface is placed under the nose of the patient, the nozzle being adapted to be in fluid communication with a gas delivery circuit and a gas delivery source;
wherein the nozzle is of configured to deliver a gas flow cone defined by the gas exiting the nozzle, such that when the non-sealing nasal interface is placed under the nose of the patient, the gas flow cone intersects with an internal wall of the patient's nostril airway at an intersecting point, the area inside the gas flow cone and the area within the patient's nostril airway distal to the intersecting point defining a positive pressure area wherein a laminar positive pressure flow is developed, the area outside the gas flow cone defining a negative pressure area entraining ambient air into the patient's nostril airway;
wherein a combination of gas from the gas delivery source and air entrained into the patient's nostril airway provides ventilatory support.

35. The method of claim 34, wherein the non-sealing nasal interface comprises a manifold, and wherein the manifold comprises the nozzle.

36. The method of claim 35, wherein the manifold is configured to position the nozzle at the distance away from the nostril entrance, and configured to position the nozzle at an angle relative a centerline of the nostril airway.

37. The method of claim 34, further comprising one or more sensors.

38. The method of claim 37, wherein the one or more sensors comprise a sensing channel that extends away from the nozzle toward the nose terminating in the positive pressure area.

39. The method of claim 37, wherein the one or more sensors comprise a sensing channel that extends distally away from the nozzle.

40. The method of claim 39, wherein the sensing channel extends into the nose of the patient.

41. The method of claim 39, wherein the sensing channel extends to within +/−5 mm from the nostril entrance.

42. The method of claim 34, further comprising two or more nozzles per nostril.

43. The method of claim 34, wherein the nozzle is an oval-shaped gas delivery nozzle orifice.

44. The method of claim 34, wherein the nozzle comprises an array of multiple gas delivery nozzles arranged in a circular or oval pattern.

45. The method of claim 34, further comprising a jet pump throat comprising a flow path.

46. The method of claim 45, wherein the jet pump throat is associated with a manifold, and the nozzle is associated with a jet pump throat flow path through the jet pump throat.

47. The method of claim 46, wherein the manifold comprises an entrainment port in communication with the jet pump throat flow path.

48. The method of claim 34, wherein the nozzle angles inward.

49. The method of claim 48, wherein the nozzle angles inward at an angle of 1 degree to 20 degrees.

50. The method of claim 34, wherein the nozzle creates an oval shaped gas flow cone within the nostril airway.

51. The method of claim 50, wherein the nozzle is rotatably adjustable.

52. The method of claim 34, wherein the nozzle comprises at least one left nozzle and at least one right nozzle, wherein the spacing between the at least one left nozzle and the at least one right nozzle is adjustable.

53. The method of claim 52, wherein the at least one left nozzle and the at least one right nozzle are rotate-ably adjustable.

54. The method of claim 34, wherein spacing between the nostril entrance and nozzle is adjustable.

55. The method of claim 34, wherein the non-sealing nasal interface is available in different sizes, differing in nozzle spacing, nozzle rotational orientation and nozzle distance to nostril entrance.

56. The method of claim 34, wherein the negative pressure of the negative pressure area is less than ambient.

57. The method of claim 56, wherein the negative pressure of the negative pressure area is −5 cmH$_2$O to −28 cmH$_2$O.

58. The method of claim 34, wherein the positive pressure of the positive pressure area is greater than ambient.

59. The method of claim 58, wherein the positive pressure of the positive pressure area is 0.01 psi to 0.50 psi.

60. The method of claim 34, wherein the nozzle is positioned at a distance of up to 1.5 inches from the nostril entrance of the patient's nostril airway when the non-sealing nasal interface is placed under the nose of the patient.

61. The method of claim 34, wherein delivery of gas through the nozzle is synchronized with a breathing pattern of the patient.

62. The method of claim 34, wherein the gas from the gas delivery source is controlled by a wearable ventilator.

63. The method of claim 34, wherein ventilatory support comprises reducing the work of breathing to treat respiratory insufficiency.

64. The method of claim 34, wherein ventilatory support comprises elevating airway pressure to treat sleep apnea.

65. The method of claim 34, wherein the non-sealing nasal interface comprises a connector for coupling the system to a bridge of the nose and aligning the nozzle with the nostril entrance of the patient's nostril airway.

66. The method of claim 65, wherein the aligning of the nozzle with the nostril entrance of the patient's nostril airway comprises adjusting the angle of the nozzle to be in alignment with a centerline of the nostril airway.

* * * * *